United States Patent
Arnal et al.

(10) Patent No.: US 11,414,710 B2
(45) Date of Patent: Aug. 16, 2022

(54) COMPOSITIONS AND METHODS FOR DETECTING CIRCULATING TUMOR DNA

(71) Applicant: Quest Diagnostics Investments LLC, Secaucus, NJ (US)

(72) Inventors: Suzzette Arnal, San Juan Capistrano, CA (US); Taraneh Angeloni, San Juan Capistrano, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 228 days.

(21) Appl. No.: 16/474,533

(22) PCT Filed: Dec. 27, 2017

(86) PCT No.: PCT/US2017/068483
§ 371 (c)(1),
(2) Date: Jun. 27, 2019

(87) PCT Pub. No.: WO2018/125892
PCT Pub. Date: Jul. 5, 2018

(65) Prior Publication Data
US 2019/0330704 A1    Oct. 31, 2019

Related U.S. Application Data

(60) Provisional application No. 62/439,574, filed on Dec. 28, 2016.

(51) Int. Cl.
*C12Q 1/68* (2018.01)
*C12Q 1/6886* (2018.01)
(Continued)

(52) U.S. Cl.
CPC ......... *C12Q 1/6886* (2013.01); *C12Q 1/6806* (2013.01); *C12Q 1/6855* (2013.01); *C12Q 2525/101* (2013.01); *C12Q 2525/155* (2013.01); *C12Q 2525/191* (2013.01); *C12Q 2531/113* (2013.01); *C12Q 2535/122* (2013.01); *C12Q 2563/179* (2013.01)

(58) Field of Classification Search
CPC ....................................................... C12Q 1/68
USPC ............................................................ 435/6
See application file for complete search history.

(56) References Cited

U.S. PATENT DOCUMENTS

| 2014/0155274 A1* | 6/2014 | Xie | C12Q 1/6853 |
| | | | 506/2 |
| 2015/0275289 A1* | 10/2015 | Otwinowski | C12Q 1/6844 |
| | | | 506/2 |
| 2017/0211140 A1* | 7/2017 | Schmitt | C12Q 1/6869 |

FOREIGN PATENT DOCUMENTS

| WO | WO-2008/015396 A2 | 2/2008 |
| WO | WO-2013/142389 A1 | 9/2013 |

(Continued)

OTHER PUBLICATIONS

Varley et al., Dynamic DNA methylation across diverse human cell lines and tissues, Genome Res. Mar. 2013;23(3):555-67. doi: 10.1101/gr.147942.112. Epub Jan. 16, 2013.*

(Continued)

*Primary Examiner* — Aaron A Priest
(74) *Attorney, Agent, or Firm* — Foley & Lardner LLP

(57) ABSTRACT

The present technology provides polynucleotide compositions and methods of using the same to detect circulating tumor DNA (ctDNA) in a patient. Kits for use in practicing the methods are also provided.

18 Claims, 9 Drawing Sheets
Specification includes a Sequence Listing.

(51) Int. Cl.
  *C12Q 1/6806* (2018.01)
  *C12Q 1/6855* (2018.01)

(56) References Cited

FOREIGN PATENT DOCUMENTS

| WO | WO-2014/130890 | 8/2014 |
| WO | WO-2014/151117 A1 | 9/2014 |
| WO | WO-2016/176091 A1 | 11/2016 |

OTHER PUBLICATIONS

Schiemer, Illumina TruSeq DNA Adapters De-Mystified, Tufts Univ. Core Facility, Aug. 4, 2011.*
Supplementary European Search Report dated Dec. 7, 2020 in EP 17887560.5.
Wilkie, Gavin, "Illumina adapter and primer sequences," Bioinformatics I/O, Jan. 26, 2015, 10 pages.
International Search Report and Written Opinion Received in International Application No. PCT/US2017/068483 dated Jun. 6, 2018.
Wilkie, G., Illumina Adapter and Primer Sequences, Bioinformatics I/O, Jan. 26, 2015, pp. 2-4.

* cited by examiner

Unligated cfDNA

SEQUENCE LISTING

```
<160> NUMBER OF SEQ ID NOS: 100

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tacactcttt ccctacacga cgctcttccg atctagctgc agtagctgac t            51

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtcagctact gcagctagat cggaagagca cacgtctgaa ctccagtcac              50

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
```
tacactcttt ccctacacga cgctcttccg atcttgatga tgatactgac t        51

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtcagtatca tcatcaagat cggaagagca cacgtctgaa ctccagtcac           50

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tacactcttt ccctacacga cgctcttccg atcttcgact gtcgagtgac t        51

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtcactcgac agtcgaagat cggaagagca cacgtctgaa ctccagtcac           50

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tacactcttt ccctacacga cgctcttccg atctgtactc tagctatgac t        51

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtcatagcta gagtacagat cggaagagca cacgtctgaa ctccagtcac           50

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tacactcttt ccctacacga cgctcttccg atctcagagc actcgttgac t        51

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtcaacgagt gctctgagat cggaagagca cacgtctgaa ctccagtcac            50

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tacactcttt ccctacacga cgctcttccg atctcatgcg atagtctgac t          51

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtcagactat cgcatgagat cggaagagca cacgtctgaa ctccagtcac            50

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tacactcttt ccctacacga cgctcttccg atcttcatca gtcgagtgac t          51

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtcactcgac tgatgaagat cggaagagca cacgtctgaa ctccagtcac            50

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tacactcttt ccctacacga cgctcttccg atctaatcag cggtattgac t          51

```
<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtcaataccg ctgattagat cggaagagca cacgtctgaa ctccagtcac        50

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tacactcttt ccctacacga cgctcttccg atctagcata ctactgtgac t       51

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtcacagtag tatgctagat cggaagagca cacgtctgaa ctccagtcac        50

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tacactcttt ccctacacga cgctcttccg atctgctgat acacgttgac t       51

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtcaacgtgt atcagcagat cggaagagca cacgtctgaa ctccagtcac        50

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tacactcttt ccctacacga cgctcttccg atctctctgt cacacgtgac t       51
```

```
<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtcacgtgtg acagagagat cggaagagca cacgtctgaa ctccagtcac                50

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tacactcttt ccctacacga cgctcttccg atctgctacg tcatcatgac t             51

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtcatgatga cgtagcagat cggaagagca cacgtctgaa ctccagtcac                50

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tacactcttt ccctacacga cgctcttccg atctgcagat gtcacttgac t             51

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtcaagtgac atctgcagat cggaagagca cacgtctgaa ctccagtcac                50

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tacactcttt ccctacacga cgctcttccg atctactcac agctagtgac t             51

<210> SEQ ID NO 28
```

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtcactagct gtgagtagat cggaagagca cacgtctgaa ctccagtcac            50

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tacactcttt ccctacacga cgctcttccg atctctcgct catgtatgac t           51

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtcatacatg agcgagagat cggaagagca cacgtctgaa ctccagtcac            50

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tacactcttt ccctacacga cgctcttccg atcttagctg cactagtgac t           51

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtcactagtg cagctaagat cggaagagca cacgtctgaa ctccagtcac            50

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tacactcttt ccctacacga cgctcttccg atctcagttc gagctatgac t           51

<210> SEQ ID NO 34
<211> LENGTH: 50

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtcatagctc gaactgagat cggaagagca cacgtctgaa ctccagtcac         50

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tacactcttt ccctacacga cgctcttccg atcttgcatg actcgctgac t        51

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtcagcgagt catgcaagat cggaagagca cacgtctgaa ctccagtcac         50

<210> SEQ ID NO 37
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tacactcttt ccctacacga cgctcttccg atctgtgtac tgtacatgac t        51

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtcatgtaca gtacacagat cggaagagca cacgtctgaa ctccagtcac         50

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tacactcttt ccctacacga cgctcttccg atctactaga gtctgatgac t        51

<210> SEQ ID NO 40
<211> LENGTH: 50
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 40
gtcatcagac tctagtagat cggaagagca cacgtctgaa ctccagtcac        50

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
tacactcttt ccctacacga cgctcttccg atctagagtg cgtgtctgac t        51

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
gtcagacacg cactctagat cggaagagca cacgtctgaa ctccagtcac        50

<210> SEQ ID NO 43
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
tacactcttt ccctacacga cgctcttccg atcttacgca tcagattgac t        51

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
gtcaatctga tgcgtaagat cggaagagca cacgtctgaa ctccagtcac        50

<210> SEQ ID NO 45
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
tacactcttt ccctacacga cgctcttccg atctctgcat gacagttgac t        51

<210> SEQ ID NO 46
<211> LENGTH: 50
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 46
gtcaactgtc atgcagagat cggaagagca cacgtctgaa ctccagtcac        50

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tacactcttt ccctacacga cgctcttccg atctgtacga tctcactgac t       51

<210> SEQ ID NO 48
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtcagtgaga tcgtacagat cggaagagca cacgtctgaa ctccagtcac        50

<210> SEQ ID NO 49
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 tgact                                                          5

<210> SEQ ID NO 50
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50 gtca                                                           4

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agctgcagta gc                                                  12

<210> SEQ ID NO 52
<211> LENGTH: 12
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 52
tgatgatgat ac                                                          12

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tcgactgtcg ag                                                          12

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtactctagc ta                                                          12

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cagagcactc gt                                                          12

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
catgcgatag tc                                                          12

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tcatcagtcg ag                                                          12

<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
aatcagcggt at                                                              12

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agcatactac tg                                                              12

<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gctgatacac gt                                                              12

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctctgtcaca cg                                                              12

<210> SEQ ID NO 62
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gctacgtcat ca                                                              12

<210> SEQ ID NO 63
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gcagatgtca ct                                                              12

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
actcacagct ag                                                         12

<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ctcgctcatg ta                                                         12

<210> SEQ ID NO 66
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tagctgcact ag                                                         12

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagttcgagc ta                                                         12

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgcatgactc gc                                                         12

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gtgtactgta ca                                                         12

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 70
actagagtct ga                                                        12

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
agagtgcgtg tc                                                        12

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tacgcatcag at                                                        12

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctgcatgaca gt                                                        12

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gtacgatctc ac                                                        12

<210> SEQ ID NO 75
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gctactgcag ct                                                        12

<210> SEQ ID NO 76
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
```
gtatcatcat ca                                                           12

<210> SEQ ID NO 77
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ctcgacagtc ga                                                           12

<210> SEQ ID NO 78
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tagctagagt ac                                                           12

<210> SEQ ID NO 79
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
acgagtgctc tg                                                           12

<210> SEQ ID NO 80
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gactatcgca tg                                                           12

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctcgactgat ga                                                           12

<210> SEQ ID NO 82
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ataccgctga tt                                                           12

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cagtagtatg ct                                                           12

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
acgtgtatca gc                                                           12

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cgtgtgacag ag                                                           12

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgatgacgta gc                                                           12

<210> SEQ ID NO 87
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agtgacatct gc                                                           12

<210> SEQ ID NO 88
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ctagctgtga gt                                                           12

<210> SEQ ID NO 89
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tacatgagcg ag                                                         12

<210> SEQ ID NO 90
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ctagtgcagc ta                                                         12

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tagctcgaac tg                                                         12

<210> SEQ ID NO 92
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gcgagtcatg ca                                                         12

<210> SEQ ID NO 93
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgtacagtac ac                                                         12

<210> SEQ ID NO 94
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tcagactcta gt                                                         12

<210> SEQ ID NO 95
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gacacgcact ct                                                              12

<210> SEQ ID NO 96
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
atctgatgcg ta                                                              12

<210> SEQ ID NO 97
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
actgtcatgc ag                                                              12

<210> SEQ ID NO 98
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gtgagatcgt ac                                                              12

<210> SEQ ID NO 99
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(33)
<223> OTHER INFORMATION: a, c, t, g, unknown or other

<400> SEQUENCE: 99
caagcagaag acggcatacg agatnnnnnn nnngtgactg gagttcagac gtgtgc              56

<210> SEQ ID NO 100
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 100
aatgatacgg cgaccaccga gatctacact ctttccctac acgacgc                              47
```

COMPOSITIONS AND METHODS FOR DETECTING CIRCULATING TUMOR DNA

CROSS REFERENCE TO RELATED APPLICATIONS

This application is the U.S. National Stage of PCT/US17/68483, filed Dec. 27, 2017, which claims the benefit of and priority to U.S. Provisional Appl. No. 62/439,574, filed Dec. 28, 2016, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 26, 2019, is named 034827-1620 SL.txt and is 23,863 bytes in size.

TECHNICAL FIELD

The present technology relates to polynucleotide adapter compositions and methods of using the same to detect circulating tumor DNA (ctDNA) in a sample, such as, for example, a cell-free nucleic acid sample obtained from a subject. Kits for use in practicing the methods are also provided.

BACKGROUND

The following description of the background of the present technology is provided simply as an aid in understanding the present technology and is not admitted to describe or constitute prior art to the present technology.

Tumors continually shed DNA into the circulation (ctDNA), where it is readily accessible (Stroun et al., *Eur J Cancer Clin Oncol* 23:707-712 (1987)). Analysis of such cancer-derived cell-free DNA (cfDNA) has the potential to revolutionize cancer detection, tumor genotyping, and disease monitoring. For example, noninvasive access to tumor-derived DNA via liquid biopsies is particularly attractive for solid tumors. However, in most early- and many advanced-stage solid tumors, ctDNA blood levels are extremely low (Bettegowda, C. et al., *Sci. Transl. Med.* 6:224ra24 (2014); Newman, A. M. et al., *Nat. Med.* 20:548-554 (2014)), thus complicating ctDNA detection and analysis. Several factors influence ctDNA detection limits, but recovery of cfDNA molecules and non-biological errors introduced during library preparation and sequencing limit analytical sensitivity and continue to represent a major obstacle for ultrasensitive ctDNA profiling.

Thus, there is a need for more sensitive and high-throughput methods to detect and monitor tumor-derived nucleic acids in cancer patients.

SUMMARY OF THE PRESENT TECHNOLOGY

The methods and polynucleotide adapter compositions disclosed herein relate to the detection of mutations in ctDNA present in samples derived from a subject diagnosed as having, or suspected of having cancer. It is contemplated that the methods disclosed herein allow for rapid and sensitive detection and profiling of ctDNA mutations in various target nucleic acid sequences in the exons and/or introns of one or more cancer-related genes including, but not limited to ALK, BRAF, EGFR, ERBB2, KIT, KRAS, MET NRAS, NTRK1, PIK3CA, ROS1, and RET The methods disclosed herein provide for a framework for ultrasensitive ctDNA profiling achieved using accurate analytical models of detection limits. These qualities improve detection limits over previous methods for samples with limited DNA content.

In one aspect, the present disclosure provides a nucleic acid adapter comprising a first oligonucleotide strand and a second oligonucleotide strand, wherein (a) the first oligonucleotide strand (i) comprises a first proximal region and a first distal region, wherein the first proximal region comprises a first unique molecular identifier sequence and a first spacer sequence having the sequence 5' TGACT 3' (SEQ ID NO: 49), wherein the first spacer sequence is located 3' to the first unique molecular identifier sequence; and (ii) does not comprise a degenerate or semi-degenerate sequence; (b) the second oligonucleotide strand (i) comprises a second proximal region and a second distal region, wherein the second proximal region comprises a second unique molecular identifier sequence and a second spacer sequence having the sequence 5' GTCA 3' (SEQ ID NO: 50), wherein the spacer sequence is located 5' to the second unique molecular identifier; and (ii) does not comprise a degenerate or semi-degenerate sequence; (c) the first proximal region of the first oligonucleotide strand hybridizes with the second proximal region of the second oligonucleotide strand; and (d) the first distal region of the first oligonucleotide strand does not hybridize with the second distal region of the second oligonucleotide strand. In some embodiments of the nucleic acid adapter, the "T" nucleotide located at the 3' end of the first spacer sequence contains a phosphorothioate bond.

In some embodiments, the first unique molecular identifier sequence of the first oligonucleotide strand is selected from the group consisting of: 5' AGCTGCAGTAGC 3' (SEQ ID NO: 51); 5' TGATGATGATAC 3' (SEQ ID NO: 52); 5' TCGACTGTCGAG 3' (SEQ ID NO: 53); 5' GTACTCTAGCTA 3' (SEQ ID NO: 54); 5' CAGAGCACTCGT 3' (SEQ ID NO: 55); 5' CATGCGATAGTC 3' (SEQ ID NO: 56); 5' TCATCAGTCGAG 3' (SEQ ID NO: 57); 5' AATCAGCGGTAT 3' (SEQ ID NO: 58); 5' AGCATACTACTG 3' (SEQ ID NO: 59); 5' GCTGATACACGT 3' (SEQ ID NO: 60); 5' CTCTGTCACACG 3' (SEQ ID NO: 61); 5' GCTACGTCATCA 3' (SEQ ID NO: 62); 5' GCAGATGTCACT 3' (SEQ ID NO: 63); 5' ACTCACAGCTAG 3' (SEQ ID NO: 64); 5' CTCGCTCATGTA 3' (SEQ ID NO: 65); 5' TAGCTGCACTAG 3' (SEQ ID NO: 66); 5' CAGTTCGAGCTA 3' (SEQ ID NO: 67); 5' TGCATGACTCGC 3' (SEQ ID NO: 68); 5' GTGTACTGTACA 3' (SEQ ID NO: 69); 5' ACTAGAGTCTGA 3' (SEQ ID NO: 70); 5' AGAGTGCGTGTC 3' (SEQ ID NO: 71); 5' TACGCATCAGAT 3' (SEQ ID NO: 72); 5' CTGCATGACAGT 3' (SEQ ID NO: 73); and 5' GTACGATCTCAC 3' (SEQ ID NO: 74).

Additionally or alternatively, in some embodiments, the second unique molecular identifier sequence of the second oligonucleotide strand is selected from the group consisting of: 5' GCTACTGCAGCT 3' (SEQ ID NO: 75); 5' GTATCATCATCA 3' (SEQ ID NO: 76); 5' CTCGACAGTCGA 3' (SEQ ID NO: 77); 5' TAGCTAGAGTAC 3' (SEQ ID NO: 78); 5' ACGAGTGCTCTG 3' (SEQ ID NO: 79); 5' GACTATCGCATG 3' (SEQ ID NO: 80); 5' CTCGACTGATGA 3' (SEQ ID NO: 81); 5' ATACCGCTGATT 3' (SEQ ID NO: 82); 5' CAGTAGTATGCT 3' (SEQ ID NO: 83); 5' ACGTGTATCAGC 3' (SEQ ID NO: 84); 5' CGTGTGACAGAG 3' (SEQ ID NO: 85); 5' TGATGACGTAGC 3' (SEQ ID NO: 86); 5' AGTGACATCTGC 3' (SEQ ID NO: 87); 5' CTAGCTGTGAGT 3'

(SEQ ID NO: 88); 5' TACATGAGCGAG 3' (SEQ ID NO: 89); 5' CTAGTGCAGCTA 3' (SEQ ID NO: 90); 5' TAGCTCGAACTG 3' (SEQ ID NO: 91); 5' GCGAGTCATGCA 3' (SEQ ID NO: 92); 5' TGTACAGTACAC 3' (SEQ ID NO: 93); 5' TCAGACTCTAGT 3' (SEQ ID NO: 94); 5' GACACGCACTCT 3' (SEQ ID NO: 95); 5' ATCTGATGCGTA 3' (SEQ ID NO: 96); 5' ACTGTCATGCAG 3' (SEQ ID NO: 97); and 5' GTGAGATCGTAC 3' (SEQ ID NO: 98).

In some embodiments, the nucleotide sequence of the first oligonucleotide strand is selected from the group consisting of: 5' TACACTCTTTCCCTACACGACGCTCTTCCGATCTAGCTGCAGTAGCTGACT 3' (SEQ ID NO: 1); 5' TACACTCTTTCCCTACACGACGCTCTTCCGATCTTGATGATGATACTGACT 3' (SEQ ID NO: 3); 5' TACACTCTTTCCCTACACGACGCTCTTCCGATCTTCGACTGTCGAGTGACT 3' (SEQ ID NO: 5); 5' TACACTCTTTCCCTACACGACGCTCTTCCGATCTGTACTCTAGCTATGACT 3' (SEQ ID NO: 7); 5' TACACTCTTTCCCTACACGACGCTCTTCCGATCTCAGAGCACTCGTTGACT 3' (SEQ ID NO: 9); 5' TACACTCTTTCCCTACACGACGCTCTTCCGATCTCATGCGATAGTCTGACT 3' (SEQ ID NO: 11); 5' TACACTCTTTCCCTACACGACGCTCTTCCGATCTTCATCAGTCGAGTGACT 3' (SEQ ID NO: 13); 5' TACACTCTTTCCCTACACGACGCTCTTCCGATCTAATCAGCGGTATTGACT 3' (SEQ ID NO: 15); 5' TACACTCTTTCCCTACACGACGCTCTTCCGATCTAGCATACTACTGTGACT 3' (SEQ ID NO: 17); 5' TACACTCTTTCCCTACACGACGCTCTTCCGATCTGCTGATACACGTTGACT 3' (SEQ ID NO: 19); 5' TACACTCTTTCCCTACACGACGCTCTTCCGATCTCTCTGTCACACGTGACT 3' (SEQ ID NO: 21); 5' TACACTCTTTCCCTACACGACGCTCTTCCGATCTGCTACGTCATCATGACT 3' (SEQ ID NO: 23); 5' TACACTCTTTCCCTACACGACGCTCTTCCGATCTGCAGATGTCACTTGACT 3' (SEQ ID NO: 25); 5' TACACTCTTTCCCTACACGACGCTCTTCCGATCTACTCACAGCTAGTGACT 3' (SEQ ID NO: 27); 5' TACACTCTTTCCCTACACGACGCTCTTCCGATCTCTCGCTCATGTATGACT 3' (SEQ ID NO: 29); 5' TACACTCTTTCCCTACACGACGCTCTTCCGATCTAGCTGCACTAGTGACT 3' (SEQ ID NO: 31); 5' TACACTCTTTCCCTACACGACGCTCTTCCGATCTCAGTTCGAGCTATGACT 3' (SEQ ID NO: 33); 5' TACACTCTTTCCCTACACGACGCTCTTCCGATCTTGCATGACTCGCTGACT 3' (SEQ ID NO: 35); 5' TACACTCTTTCCCTACACGACGCTCTTCCGATCTGTGTACTGTACATGACT 3' (SEQ ID NO: 37); 5' TACACTCTTTCCCTACACGACGCTCTTCCGATCTACTAGAGTCTGATGACT 3' (SEQ ID NO: 39); 5' TACACTCTTTCCCTACACGACGCTCTTCCGATCTAGAGTGCGTGTCTGACT 3' (SEQ ID NO: 41); 5' TACACTCTTTCCCTACACGACGCTCTTCCGATCTTACGCATCAGATTGACT 3' (SEQ ID NO: 43); 5' TACACTCTTTCCCTACACGACGCTCTTCCGATCTCTGCATGACAGTTGACT 3' (SEQ ID NO: 45); and 5' TACACTCTTTCCCTACACGACGCTCTTCCGATCTGTACGATCTCACTGACT 3' (SEQ ID NO: 47).

Additionally or alternatively, in some embodiments, the nucleotide sequence of the second oligonucleotide strand is selected from the group consisting of: 5' GTCAGCTACTGCAGCTAGATCGGAAGAGCACACGTCTGAACTCCAGTCAC 3' (SEQ ID NO: 2); 5' GTCAGTATCATCATCAAGATCGGAAGAGCACACGTCTGAACTCCAGTCAC 3' (SEQ ID NO: 4); 5' GTCACTCGACAGTCGAAGATCGGAAGAGCACACGTCTGAACTCCAGTCAC 3' (SEQ ID NO: 6); 5' GTCATAGCTAGAGTACAGATCGGAAGAGCACACGTCTGAACTCCAGTCAC 3' (SEQ ID NO: 8); 5' GTCAACGAGTGCTCTGAGATCGGAAGAGCACACGTCTGAACTCCAGTCAC 3' (SEQ ID NO: 10); 5' GTCAGACTATCGCATGAGATCGGAAGAGCACACGTCTGAACTCCAGTCAC 3' (SEQ ID NO: 12); 5' GTCACTCGACTGATGAAGATCGGAAGAGCACACGTCTGAACTCCAGTCAC 3' (SEQ ID NO: 14); 5' GTCAATACCGCTGATTAGATCGGAAGAGCACACGTCTGAACTCCAGTCAC 3' (SEQ ID NO: 16); 5' GTCACAGTAGTATGCTAGATCGGAAGAGCACACGTCTGAACTCCAGTCAC 3' (SEQ ID NO: 18); 5' GTCAACGTGTATCAGCAGATCGGAAGAGCACACGTCTGAACTCCAGTCAC 3' (SEQ ID NO: 20); 5' GTCACGTGTGACAGAGAGATCGGAAGAGCACACGTCTGAACTCCAGTCAC 3' (SEQ ID NO: 22); 5' GTCATGATGACGTAGCAGATCGGAAGAGCACACGTCTGAACTCCAGTCAC 3' (SEQ ID NO: 24); 5' GTCAAGTGACATCTGCAGATCGGAAGAGCACACGTCTGAACTCCAGTCAC 3' (SEQ ID NO: 26); 5' GTCACTAGCTGTGAGTAGATCGGAAGAGCACACGTCTGAACTCCAGTCAC 3' (SEQ ID NO: 28); 5' GTCATACATGAGCGAGAGATCGGAAGAGCACACGTCTGAACTCCAGTCAC 3' (SEQ ID NO: 30); 5' GTCACTAGTGCAGCTAAGATCGGAAGAGCACACGTCTGAACTCCAGTCAC 3' (SEQ ID NO: 32); 5' GTCATAGCTCGAACTGAGATCGGAAGAGCACACGTCTGAACTCCAGTCAC 3' (SEQ ID NO: 34); 5' GTCAGCGAGTCATGCAAGATCGGAAGAGCACACGTCTGAACTCCAGTCAC 3' (SEQ ID NO: 36); 5' GTCATGTACAGTACACAGATCGGAAGAGCACACGTCTGAACTCCAGTCAC 3' (SEQ ID NO: 38); 5' GTCATCAGACTCTAGTAGATCGGAAGAGCACACGTCTGAACTCCAGTCAC 3' (SEQ ID NO: 40); 5' GTCAGACACGCACTCTAGATCGGAAGAGCACACGTCTGAACTCCAGTCAC 3' (SEQ ID NO: 42); 5' GTCAATCTGATGCGTAAGATCGGAAGAGCACACGTCTGAACTCCAGTCAC 3' (SEQ ID NO: 44); 5' GTCAACTGTCATGCAGAGATCGGAAGAGCACACGTCTGAACTCCAGTCAC 3' (SEQ ID NO: 46); and 5' GTCAGTGAGATCGTACAGATCGGAAGAGCACACGTCTGAACTCCAGTCAC 3' (SEQ ID NO: 48).

In certain embodiments of the nucleic acid adapter, the 5' end of the first oligonucleotide strand is labelled with biotin. In other embodiments of the nucleic acid adapter, the 3' end of the second oligonucleotide strand is labelled with biotin. In some embodiments, the nucleic acid adapter is used to sequence a double-stranded target nucleic acid molecule selected from the group consisting of double-stranded DNA or double-stranded RNA. The double-stranded DNA may be sheared genomic DNA, or cell-free DNA.

In any of the above embodiments, the nucleic acid adapter of the present technology further comprises at least two PCR primer binding sites, at least two sequencing primer binding sites, or any combination thereof. Additionally or alternatively, in some embodiments, the nucleic acid adapter of the present technology further comprises a sample-specific barcode sequence, wherein the sample-specific barcode sequence comprises 2-20 nucleotides.

In another aspect, the present disclosure provides a method for detecting at least one mutation in a double-stranded circulating tumor DNA (ctDNA) molecule present in a sample obtained from a patient comprising (a) ligating a plurality of Y-shaped adapters to both ends of the double-stranded ctDNA molecule to form a double-stranded adapter-ctDNA complex, each Y-shaped adapter comprising a first oligonucleotide strand and a second oligonucleotide strand, wherein the sequence of the first oligonucleotide strand and the sequence of the second oligonucleotide strand are selected from the group consisting of SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; and SEQ ID NO: 47 and SEQ ID NO: 48; (b) amplifying both strands of the adapter-ctDNA complex to produce first amplicons and second amplicons, wherein the first amplicons are derived from the first oligonucleotide strand, and the second amplicons are derived from the second oligonucleotide strand; (c) sequencing the first and second amplicons; (d) detecting at least one mutation in the double-stranded ctDNA molecule, when a mutation detected in the first amplicons is consistent with a mutation detected in the second amplicons. In some embodiments of the method, the patient is diagnosed with ovarian cancer, breast cancer, colon cancer, lung cancer, prostate cancer, gastric cancer, pancreatic cancer, cervical cancer, liver cancer, bladder cancer, cancer of the urinary tract, thyroid cancer, renal cancer, carcinoma, melanoma, head and neck cancer, or brain cancer.

In some embodiments, the method further comprises enriching the first amplicons and second amplicons with a plurality of bait sequences, wherein the plurality of bait sequences comprises at least one gene region that corresponds to each of a plurality of cancer-related genes. The plurality of cancer-related genes may comprise ALK, BRAF, EGFR, ERBB2, KIT, KRAS, MET, NRAS, NTRK1, PIK3CA, ROS1, and RET Additionally or alternatively, in some embodiments of the method, the plurality of bait sequences are RNA baits, DNA baits, or a mixture of RNA baits and DNA baits. In certain embodiments, the plurality of bait sequences comprises a 1:1 mixture of RNA baits and DNA baits. In other embodiments, the plurality of bait sequences comprises a mixture of RNA baits and DNA baits having a ratio of 2:1, 1.5:1, 0.75:1 or 0.5:1.

In certain embodiments of the method, both of the 3' ends of the double-stranded ctDNA molecule further comprise an "A"-overhang.

In any of the above embodiments, each Y-shaped adapter further comprises at least two sequencing primer binding sites. Additionally or alternatively, in some embodiments, each Y-shaped adapter further comprises a patient-specific barcode sequence, wherein the patient-specific barcode sequence comprises 2-20 nucleotides. Each Y-shaped adapter of the present technology may be labelled with biotin.

In some embodiments of the method, the sample comprises no more than 5 ng of cell-free DNA. In other embodiments, the sample comprises at least 6-30 ng of cell-free DNA. In certain embodiments, the sample is whole blood, serum, plasma, synovial fluid, lymphatic fluid, ascites fluid, or interstitial fluid.

Also disclosed herein, are kits comprising one or more Y-shaped nucleic acid adapters comprising at least one sequence selected from among SEQ ID NOS: 1-48, and instructions for use.

DETAILED DESCRIPTION

Figure 1A:
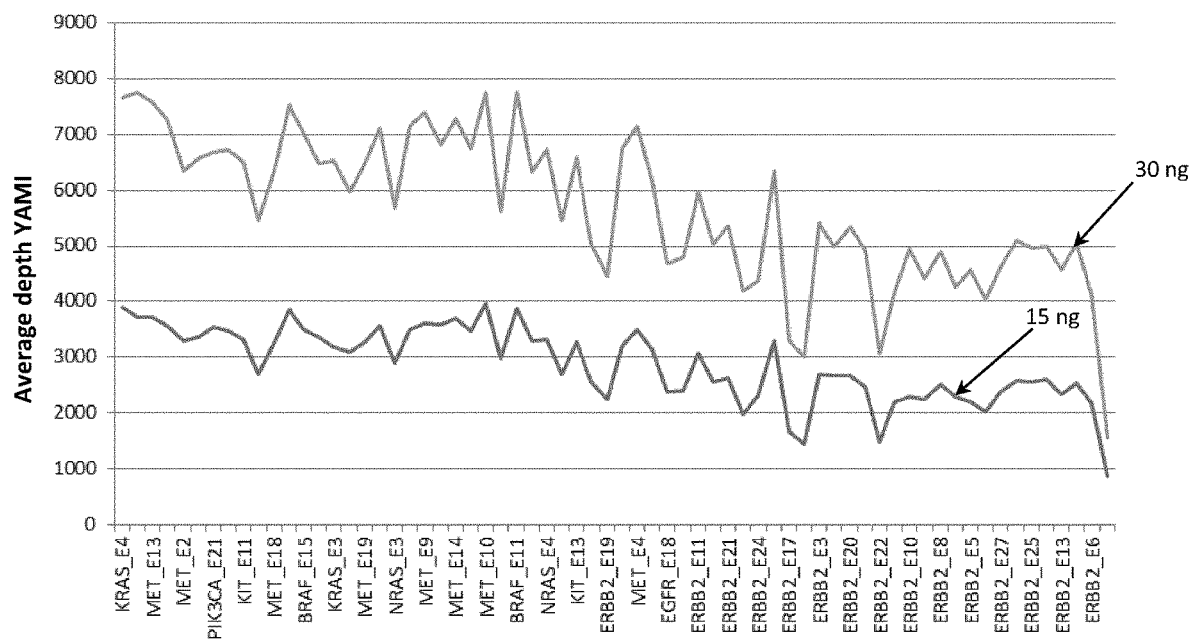
FIG. 1(a) shows the deduped coverage of certain exon or intron regions of several cancer-related genes at varying cfDNA input levels (15 ng or 30 ng) using the Y-shaped nucleic acids adapters of the present technology (or YAMIs).

The present disclosure provides polynucleotide adapter compositions and methods for detecting mutations in cell-free nucleic acids, for example ctDNA present in samples derived from subjects diagnosed as having, or suspected of having cancer. Kits for use in practicing the methods are also provided.

The genetic changes in cancer cells can provide a means by which cancer cells can be distinguished from normal (e.g., non-cancerous) cells. For example, cfDNA can be analyzed for the presence of genetic variation distinctive of tumor cells. However, the absolute levels of cell-free tumor DNA in such samples is often low, and the genetic variation may represent only a very small portion of the entire genome. Two important factors underlying the detection limit of all ctDNA profiling methods are the number of cfDNA molecules that are recovered and the number of mutations in a patient's tumor that are interrogated. Clinically relevant blood volumes are frequently limiting in cancer patients due to anemia, comorbidities, and poor patient performance status. Studies analyzing cfDNA from healthy controls have shown that background errors were increasingly evident below allele fractions of ~0.2% and >50% of sequenced genomic positions had artifacts under an allele fraction of 0.02% (Newman et al., *Nat Biotechnol.* 34(5):547-55 (2016)).

Although a variety of methods for reducing sequencing-related artifacts have been reported, a common approach involves tagging individual DNA molecules with unique identifiers (UIDs, also known as molecular barcodes) (Jabara et al., *Proc. Natl. Acad. Sci. USA* 108, 20166-20171 (2011); Kinde et al., *Proc. Natl. Acad. Sci. USA* 108, 9530-9535 (2011); Schmitt, M. W. et al., *Proc. Natl. Acad. Sci. USA* 109, 14508-14513 (2012); Kennedy, S. R. et al., *Nat. Protoc.* 9, 2586-2606 (2014); Kukita, Y. et al., *DNA Res.* 22, 269-277 (2015); Schmitt, M. W. et al., *Nat. Methods* 12, 423-425 (2015)). Such barcodes enable the precise tracking of individual molecules, making it possible to distinguish authentic somatic mutations arising in vivo from artifacts introduced ex vivo.

Recent strategies can track double-stranded 'duplex' DNA molecules present in the original sample (Kennedy, S. R. et al., *Nat. Protoc.* 9, 2586-2606 (2014); Gregory, M. T. et al., *Nucleic Acids Res.* 44, e22 (2016); Schmitt, M. W. et al., *Nat. Methods* 12, 423-425 (2015)). Although duplex barcoding achieves better error suppression than single-stranded barcoding methods, it is relatively inefficient (Kennedy, S. R. et al., *Nat. Protoc.* 9, 2586-2606 (2014)) and thus suboptimal for the limited cfDNA quantities obtainable in a clinical setting. Previous studies have reported that library construction methods that involve the use of Y-shaped nucleic acid adapters can result in widespread adapter-dimer artifact formation, thus making them unsuitable for applications that utilize low amounts of nucleic acid starting material. Bennett et al., *BioTechniques* 56:289-300 (2014). Indeed, the overall performance of the adapters described in Kennedy et al. (2014) during the ligation stage of library preparation was poor, thus limiting their use with respect to detecting mutations in ctDNA. (Newman et al., *Nat Biotechnol.* 34(5):547-55 (2016)); see also FIG. 1(*b*) and FIG. 3(*a*)).

In contrast, the polynucleotide adapter compositions of the present technology increase ligation efficiency by approximately 20% (Table 1), thereby promoting efficient recovery of ctDNA from samples containing limited cfDNA inputs. Further, the methods of the present technology generated approximately 500-1800 single strand consensus reads (SSC S) within target gene regions from cfDNA input levels as low as 5 ng. See FIG. 7. Accordingly, the methods of the present technology show improved analytical sensitivity when detecting mutations in ctDNA present in samples derived from a subject diagnosed as having, or suspected of having cancer.

Definitions

As used herein, the term "about" in reference to a number is generally taken to include numbers that fall within a range of 1%-5% in either direction (greater than or less than) of the number unless otherwise stated or otherwise evident from the context.

As used herein, the terms "amplify" or "amplification" with respect to nucleic acid sequences, refer to methods that increase the representation of a population of nucleic acid sequences in a sample. Nucleic acid amplification methods, such as PCR, isothermal methods, rolling circle methods, etc., are well known to the skilled artisan. Copies of a particular nucleic acid sequence generated in vitro in an amplification reaction are called "amplicons" or "amplification products".

The term "adapter" refers to a short, chemically synthesized, nucleic acid sequence which can be used to ligate to the 3' or 5' end of a nucleic acid sequence in order to facilitate attachment to another molecule. The adapter can be single-stranded or double-stranded. An adapter can incorporate a short (e.g., less than 55 base pairs) sequence useful for PCR amplification or sequencing. The adapter can comprise known sequences, degenerate sequences, or both. A double-stranded adapter may comprise two hybridizable strands. Alternatively, a double-stranded adapter can comprise a hybridizable portion and a non-hybridizable portion. The non-hybridizable portion of a double-stranded adapter comprises two single-stranded regions that are not hybridizable to each other. Within the non hybridizable portion, the strand containing an unhybridized 5'-end is referred to as the 5'-strand and the strand containing an unhybridized 3'-end is referred to as the 3'-strand. In some embodiments, the double-stranded adapter has a hybridizable portion at one end of the adapter and a non-hybridizable portion at the opposite end of the adapter. In some embodiments, the non-hybridizable portion of the double-stranded adapter may be open (Y-shaped adapter).

The term "barcode" refers to a sequence of nucleotides within a polynucleotide that is used to identify a nucleic acid molecule. For example, a barcode can be used to identify molecules when the molecules from several groups are combined for processing or sequencing in a multiplexed fashion. A barcode can be located at a certain position within a polynucleotide (e.g., at the 3'-end, 5'-end, or middle of the polynucleotide) and can comprise sequences of any length (e.g., 1-100 or more nucleotides). Additionally, a barcode can comprise one or more pre-defined sequences. The term "pre-defined" means that sequence of a barcode is predetermined or known prior to identifying or without the need to identify the entire sequence of the nucleic acid comprising the barcode. In some cases, pre-defined barcodes can be attached to nucleic acids for sorting the nucleic acids into groups. In some embodiments, a barcode can comprise artificial sequences, e.g., designed or engineered sequences that are not present in the unaltered (wild-type) genome of a subject. In other embodiments, a barcode can comprise an endogenous sequence, e.g., sequences that are present in the unaltered (wildtype) genome of a subject. In certain embodiments, a barcode can be an endogenous barcode. An endogenous barcode can be a sequence of a genomic nucleic acid, where the sequence is used as a barcode or identifier for the genomic nucleic acid. One or more sequences of the genomic DNA fragment can be an endogenous barcode. Different types of barcodes can be used in combination. For example, an endogenous genomic nucleic acid fragment can be attached to an artificial sequence, which can be used as a unique identifier of the genomic nucleic acid fragment. A "sample-specific barcode" or "patient barcode" refers to a polynucleotide sequence that is used to identify the origin or source of a nucleic acid molecule. For example, a sequence of "AAAA" can be attached to identify nucleic acids isolated from Patient A.

As used herein, the terms "random sequence" or "degenerate sequence" refer to a sequence not having a precise definition.

"Bait", as used herein, is a type of hybrid capture reagent that retrieves target nucleic acid sequences for sequencing. A bait can be a nucleic acid molecule, e.g., a DNA or RNA molecule, which can hybridize to (e.g., be complementary to), and thereby allow capture of a target nucleic acid. In one embodiment, a bait is an RNA molecule (e.g., a naturally-occurring or modified RNA molecule); a DNA molecule (e.g., a naturally-occurring or modified DNA molecule), or a combination thereof. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

The terms "cancer" or "tumor" are used interchangeably and refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell. As used herein, the term "cancer cells" includes precancerous (e.g., benign), malignant, pre-metastatic, metastatic, and non-metastatic cells. Cancers of virtually every tissue are known to those of skill in the art, including solid tumors such as carcinomas, sarcomas, glioblastomas, melanomas, lymphomas, myelomas, etc., and circulating cancers such as leukemias. Examples of cancer include, but are not limited to, ovarian cancer, breast cancer, colon cancer, lung cancer, prostate cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. The phrase "cancer burden" or "tumor burden" refers to the quantity of cancer cells or tumor volume in a subject. Reducing cancer burden accordingly may refer to reducing the number of cancer cells, or the tumor volume in a subject. The term "cancer cell" refers to a cell that exhibits cancer-like properties, e.g., uncontrollable reproduction, resistance to anti-growth signals, ability to metastasize, and loss of ability to undergo programmed cell death (e.g., apoptosis) or a cell that is derived from a cancer cell, e.g., clone of a cancer cell.

The term "cell-free DNA (cfDNA)" refers to DNA in a sample that when collected, was not contained within a cell. cfDNAs can comprise both normal cell and cancer cell-derived DNA. cfDNA is commonly obtained from blood or plasma ("circulation"). cfDNAs may be released into the circulation through secretion or cell death processes, e.g., cellular necrosis or apoptosis. A fraction of cfDNA may include ctDNA.

The term "circulating tumor DNA (ctDNA)" refers to the fraction of cell-free DNA (cfDNA) in a sample that originates from a tumor.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA).

Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

As used herein, a "control" is an alternative sample used in an experiment for comparison purpose. A control can be "positive" or "negative." A "control nucleic acid sample" or "reference nucleic acid sample" as used herein, refers to nucleic acid molecules from a control or reference sample. In certain embodiments, the reference or control nucleic acid sample is a wild type or a non-mutated DNA or RNA sequence. In certain embodiments, the reference nucleic acid sample is purified or isolated (e.g., it is removed from its natural state).

The term "deduping" refers to a method comprising grouping nucleic acid sequences into groups comprising progeny of a single molecule originally present in the sample. The original molecule and its progeny are characterized by the same unique molecular barcode (UID). Deduping further comprises analysis of the sequences of the progeny molecules to indirectly determine the sequence of the original molecule with a reduced rate of errors.

"Detecting" as used herein refers to determining the presence of a mutation in a nucleic acid of interest in a sample. Detection does not require the method to provide 100% sensitivity.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

The term "gene region" can refer to a range of sequences within a gene or surrounding a gene, e.g., an intron, an exon, a promoter, a 3' untranslated region etc.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

The term "hybridizable" means that two polynucleotide strands of a nucleic acid are complementary at one or more nucleotide positions, e.g., the nitrogenous bases of the two polynucleotide strands can form two or more Crick-Watson hydrogen bonds. For example, if a polynucleotide comprises 5' ATGC 3', it is hybridizable to the sequence 5' GCAT 3'. Under some experimental conditions, if a polynucleotide comprises 5' GGGG 3', it can also be hybridizable to the sequences 5'CCAC 3' and 5' CCCA 3', which are not perfectly complementary.

The term "non-hybridizable" means that two polynucleotide strands of a nucleic acid are non-complementary, e.g., nitrogenous bases of the two separate polynucleotide strands do not form two or more Crick-Watson hydrogen bonds under stringent hybridization conditions.

As used herein, the terms "individual", "patient", or "subject" are used interchangeably and refer to an individual organism, a vertebrate, a mammal, or a human. In a preferred embodiment, the individual, patient or subject is a human.

As used herein, the term "library" refers to a collection of nucleic acid sequences, e.g., a collection of nucleic acids derived from whole genomic, subgenomic fragments, cDNA, cDNA fragments, cfDNA, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, for sequencing, or for cloning into a vector.

The library can comprise a collection of nucleic acid sequences, e.g., a target nucleic acid sequence (e.g., a tumor nucleic acid sequence), a reference nucleic acid sequence, or a combination thereof. In some embodiments, the nucleic acid sequences of the library can be derived from a single subject. In other embodiments, a library can comprise nucleic acid sequences from more than one subject (e.g., 2, 3, 4, 5, 6, 7, 8, 9, 10, 20, 30 or more subjects). In some embodiments, two or more libraries from different subjects can be combined to form a library having nucleic acid sequences from more than one subject. In one embodiment, the subject has, or is at risk of having, a cancer or tumor.

A "library nucleic acid sequence" refers to a nucleic acid molecule, e.g., DNA, RNA, or a combination thereof, that is a member of a library. In some embodiments, a library nucleic acid sequence is a DNA molecule, e.g., genomic DNA, cfDNA, or cDNA. In some embodiments, a library nucleic acid sequence is fragmented, e.g., sheared or enzymatically prepared, genomic DNA. In certain embodiments, the library nucleic acid sequences comprise a sequence from a subject and a sequence not derived from the subject, e.g., adapter sequence, a primer sequence, or other sequences that allow for identification, e.g., "barcode" sequences.

The term "ligating" refers to connecting two molecules by chemical bonds to generate a new molecule. For example, ligating an adapter polynucleotide to another polynucleotide can refer to forming chemical bonds between the adapter and the polynucleotide (e.g., using a ligase or any other method) to generate a single new molecule comprising the adapter and the polynucleotide.

The term "multiplex PCR" as used herein refers to amplification of two or more PCR products or amplicons which are each primed using a distinct primer pair.

The term "mutation" refers to a genetic alteration in the genome of an organism or a cell. For example, mutations of interest can be changes relative to the germline of an organism, e.g., cancer cell-specific changes. Mutations may include single nucleotide variants (SNV), copy number variants (CNV), insertions, deletions, and rearrangements (e.g., fusions).

"Next-generation sequencing or NGS" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. *Nature Biotechnology Reviews* 11:31-46 (2010).

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. One or more bases of the oligonucleotide may also be modified to include a phosphorothioate bond (e.g., one of the two oxygen atoms in the phosphate backbone which is not involved in the internucleotide bridge, is replaced by a sulfur atom) to increase resistance to nuclease degradation. Oligonucleotides of the method which function as primers or probes are generally at least about 10-15 nucleotides long and more preferably at least about 15 to 55 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

The term "polynucleotide" refers to a biopolymer that comprises one or more nucleotide monomers (natural or non-natural) covalently bonded in a chain. In some embodiments, a polynucleotide can have a sequence comprising a genomic nucleic acid sequence. In other embodiments, a polynucleotide can have an artificial sequence (e.g., a sequence not found in genomic nucleic acids). A polynucleotide can comprise genomic nucleic acid sequence and/or an artificial sequence. An artificial sequence may or may not contain non-natural nucleotides.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of dsDNA. A "reverse primer" anneals to the sense-strand of dsDNA.

As used herein, "primer pair" refers to a forward and reverse primer pair (i.e., a left and right primer pair) that can be used together to amplify a given region of a nucleic acid of interest.

As used herein, a "sample" refers to a substance that is being assayed for the presence of a mutation in a nucleic acid of interest. Processing methods to release or otherwise make available a nucleic acid for detection are well known in the art and may include steps of nucleic acid manipulation. A biological sample may be a body fluid or a tissue sample isolated from a subject. In some cases, a biological sample may consist of or comprise whole blood, platelets, red blood cells, white blood cells, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, endothelial cells, synovial fluid, lymphatic fluid, ascites fluid, interstitial or extracellular fluid and the like. The term "sample" may also encompass the fluid in spaces between cells, including gingival crevicular fluid, bone marrow, cerebrospinal fluid (CSF), saliva, mucus, sputum, semen, sweat, urine, or any other bodily fluids. Samples can be obtained from a subject by any means including, but not limited to, venipuncture, excretion, ejaculation, massage, biopsy, needle aspirate, lavage, scraping, surgical incision, or intervention or other means known in the art. A blood sample can be whole blood or any fraction thereof, including blood cells (red blood cells, white blood cells or leucocytes, and platelets), serum and plasma. Whole blood samples of about 0.5 to 5 ml collected with EDTA, ACD or heparin as anti-coagulant are suitable.

As used herein, a "selector" refers to a plurality of oligonucleotides or probes that hybridize with one or more genomic regions. In some embodiments, the one or more genomic regions may be associated with diseases, e.g., cancers.

The term "sensitivity," as used herein in reference to the methods of the present technology, is a measure of the ability of a method to detect a preselected sequence variant in a heterogeneous population of sequences. A method has a sensitivity of S % for variants of F if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%).

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "target sequence" and "target nucleic acid sequence" refer to a specific nucleic acid sequence to be detected and/or quantified in the sample to be analyzed.

Nucleic Acid Adapters of the Present Technology

Provided herein are polynucleotide adapter compositions that are useful for identifying or analyzing nucleic acids. In some embodiments, the nucleic acid adapters of the present technology are Y-shaped adapters.

The present technology provides a plurality of Y-shaped adapters, wherein each Y-shaped adapter comprises a hybridizable portion at one end (proximal end) of the Y-shaped adapter and a non-hybridizable portion at the opposite end (distal end) of the Y-shaped adapter, wherein the hybridizable portion comprises a unique identifiable double-stranded barcode sequence of at least 6-12 base pairs. The nucleic acid adapters disclosed herein can be attached to the one or more nucleic acids (e.g., cfDNA) through the hybridizable (double-stranded) portion of the adapters.

Also provided herein are a plurality of Y-shaped adapters, wherein each Y-shaped adapter comprises a hybridizable portion at one end (proximal end) of the Y-shaped adapter and a non-hybridizable portion at the opposite end (distal end) of the Y-shaped adapter, and wherein each Y-shaped adapter comprises a patient barcode of at least two nucleotides.

The nucleic acid adapters of the present technology comprise a first oligonucleotide strand and a second oligonucleotide strand, wherein (a) the first oligonucleotide strand (i) comprises a first proximal region and a first distal region, wherein the first proximal region comprises a first unique molecular identifier sequence and a first spacer sequence having the sequence 5' TGACT 3' (SEQ ID NO: 49), wherein the first spacer sequence is located 3' to the first unique molecular identifier sequence; and (ii) does not comprise a degenerate or semi-degenerate sequence; (b) the second oligonucleotide strand (i) comprises a second proximal region and a second distal region, wherein the second proximal region comprises a second unique molecular identifier sequence and a second spacer sequence having the sequence 5' GTCA 3' (SEQ ID NO: 50), wherein the spacer sequence is located 5' to the second unique molecular identifier; and (ii) does not comprise a degenerate or semi-degenerate sequence; (c) the first proximal region of the first oligonucleotide strand hybridizes with the second proximal region of the second oligonucleotide strand (i.e., the hybridizable portion of the adapter); and (d) the first distal region of the first oligonucleotide strand does not hybridize with the second distal region of the second oligonucleotide strand (i.e., the non-hybridizable portion of the adapter). In some embodiments of the nucleic acid adapter, the "T" nucleotide located at the 3' end of the first spacer sequence contains a phosphorothioate bond. In certain embodiments, the first unique molecular identifier sequence and the second unique molecular identifier sequence may comprise non-natural nucleotides, e.g., aminoallyl-uridine, iso-cytosines, isoguanine, and 2-aminopurine.

In some embodiments, the first unique molecular identifier sequence of the first oligonucleotide strand is selected from the group consisting of: 5' AGCTGCAGTAGC 3' (SEQ ID NO: 51); 5' TGATGATGATAC 3' (SEQ ID NO: 52); 5' TCGACTGTCGAG 3' (SEQ ID NO: 53); 5' GTACTCTAGCTA 3' (SEQ ID NO: 54); 5' CAGAGCACTCGT 3' (SEQ ID NO: 55); 5' CATGCGATAGTC 3' (SEQ ID NO: 56); 5' TCATCAGTCGAG 3' (SEQ ID NO: 57); 5' AATCAGCGGTAT 3' (SEQ ID NO: 58); 5' AGCATACTACTG 3' (SEQ ID NO: 59); 5' GCTGATACACGT 3' (SEQ ID NO: 60); 5' CTCTGTCACACG 3' (SEQ ID NO: 61); 5' GCTACGTCATCA 3' (SEQ ID NO: 62); 5' GCAGATGTCACT 3' (SEQ ID NO: 63); 5' ACTCACAGCTAG 3' (SEQ ID NO: 64); 5' CTCGCTCATGTA 3' (SEQ ID NO: 65); 5' TAGCTGCACTAG 3' (SEQ ID NO: 66); 5' CAGTTCGAGCTA 3' (SEQ ID NO: 67); 5' TGCATGACTCGC 3' (SEQ ID NO: 68); 5' GTGTACTGTACA 3' (SEQ ID NO: 69); 5' ACTAGAGTCTGA 3' (SEQ ID NO: 70); 5' AGAGTGCGTGTC 3' (SEQ ID NO: 71); 5' TACGCATCAGAT 3' (SEQ ID NO: 72); 5' CTGCATGACAGT 3' (SEQ ID NO: 73); and 5' GTACGATCTCAC 3' (SEQ ID NO: 74).

Additionally or alternatively, in some embodiments, the second unique molecular identifier sequence of the second oligonucleotide strand is selected from the group consisting of: 5' GCTACTGCAGCT 3' (SEQ ID NO: 75); 5' GTATCATCATCA 3' (SEQ ID NO: 76); 5' CTCGACAGTCGA 3' (SEQ ID NO: 77); 5' TAGCTAGAGTAC 3' (SEQ ID NO: 78); 5' ACGAGTGCTCTG 3' (SEQ ID NO: 79); 5' GACTATCGCATG 3' (SEQ ID NO: 80); 5' CTCGACTGATGA 3' (SEQ ID NO: 81); 5' ATACCGCTGATT 3' (SEQ ID NO: 82); 5' CAGTAGTATGCT 3' (SEQ ID NO: 83); 5' ACGTGTATCAGC 3' (SEQ ID NO: 84); 5' CGTGTGACAGAG 3' (SEQ ID NO: 85); 5' TGATGACGTAGC 3' (SEQ ID NO: 86); 5' AGTGACATCTGC 3' (SEQ ID NO: 87); 5' CTAGCTGTGAGT 3' (SEQ ID NO: 88); 5' TACATGAGCGAG 3' (SEQ ID NO: 89); 5' CTAGTGCAGCTA 3' (SEQ ID NO: 90); 5' TAGCTCGAACTG 3' (SEQ ID NO: 91); 5' GCGAGTCATGCA 3' (SEQ ID NO: 92); 5' TGTACAGTACAC 3' (SEQ ID NO: 93); 5' TCAGACTCTAGT 3' (SEQ ID NO: 94); 5' GACACGCACTCT 3' (SEQ ID NO: 95); 5' ATCTGATGCGTA 3' (SEQ ID NO: 96); 5' ACTGTCATGCAG 3' (SEQ ID NO: 97); and 5' GTGAGATCGTAC 3' (SEQ ID NO: 98).

In some embodiments, the nucleotide sequence of the first oligonucleotide strand is selected from the group consisting of: 5' TACACTCTTTCCCTACACGACGCTCTTCCGATCTAGCTGCAGTAGCTGACT 3' (SEQ ID NO: 1); 5' TACACTCTTTCCCTACACGACGCTCTTCCGATCTTGATGATGATACTGACT 3' (SEQ ID NO: 3); 5' TACACTCTTTCCCTACACGACGCTCTTCCGATCTTCGACTGTCGAGTGACT 3' (SEQ ID NO: 5); 5' TACACTCTTTCCCTACACGACGCTCTTCCGATCTGTACTCTAGCTATGACT 3' (SEQ ID NO: 7); 5' TACACTCTTTCCCTACACGACGCTCTTCCGATCTCAGAGCACTCGTTGACT 3' (SEQ ID NO: 9); 5' TACACTCTTTCCCTACACGACGCTCTTCCGATCTCATGCGATAGTCTGACT 3' (SEQ ID NO: 11); 5' TACACTCTTTCCCTACACGACGCTCTTCCGATCTTCATCAGTCGAGTGACT 3' (SEQ ID NO: 13); 5' TACACTCTTTCCCTACACGACGCTCTTCCGATCTAATCAGCGGTATTGACT 3' (SEQ ID NO: 15); 5' TACACTCTTTCCCTACACGACGCTCTTCCGATCTAGCATACTACTGTGACT 3' (SEQ ID NO: 17); 5' TACACTCTTTCCCTACACGACGCTCTTCCGATCTGCTGATACACGTTGACT 3' (SEQ ID NO: 19); 5' TACACTCTTTCCCTACACGACGCTCTTCCGATCTCTCTGTCACACGTGACT 3' (SEQ ID NO: 21); 5' TACACTCTTTCCCTACACGACGCTCTTCCGATCTGCTACGTCATCATGACT 3' (SEQ ID NO: 23); 5' TACACTCTTTCCCTACACGACGCTCTTCCGATCTGCAGATGTCACTTGACT 3' (SEQ ID NO: 25); 5' TACACTCTTTCCCTACACGACGCTCTTCCGATCTACTCACAGCTAGTGACT 3' (SEQ ID NO: 27); 5' TACACTCTTTCCCTACACGACGCTCTTCCGATCTCTCGCTCATGTATGACT 3' (SEQ ID NO: 29); 5' TACACTCTTTCCCTACACGACGCTCTTCCGATCTTAGCTGCACTAGTGACT 3' (SEQ ID NO: 31); 5' TACACTCTTTCCCTACACGACGCTCTTCC- GATCTCAGTTCGAGCTATGACT 3' (SEQ ID NO: 33); 5' TACACTCTTTCCCTACACGACGCTCTTCCGATCTTG-CATGACTCGCTGACT 3' (SEQ ID NO: 35); 5' TACACTCTTTCCCTACACGACGCTCTTCC-GATCTGTGTACTGTACATGACT 3' (SEQ ID NO: 37); 5' TACACTCTTTCCCTACACGACGCTCTTCCGATC-TACTAGAGTCTGATGACT 3' (SEQ ID NO: 39); 5' TACACTCTTTCCCTACACGACGCTCTTCC-GATCTAGAGTGCGTGTCTGACT 3' (SEQ ID NO: 41); 5' TACACTCTTTCCCTACACGACGCTCTTCCGATCT-TACGCATCAGATTGACT 3' (SEQ ID NO: 43); 5' TACACTCTTTCCCTACACGACGCTCTTCC-GATCTCTGCATGACAGTTGACT 3' (SEQ ID NO: 45); and 5' TACACTCTTTCCCTACACGACGCTCTTCC-GATCTGTACGATCTCACTGACT 3' (SEQ ID NO: 47).

Additionally or alternatively, in some embodiments, the nucleotide sequence of the second oligonucleotide strand is selected from the group consisting of: 5' GTCAGC-TACTGCAGCTAGATCGGAAGAGCACACGTCT-GAACTCCAGTCAC 3' (SEQ ID NO: 2); 5' GTCAGTAT-CATCATCAAGATCGGAAGAGCACACGTCTGAACT CCAGTCAC 3' (SEQ ID NO: 4); 5' GTCACTCGACAGTCGAAGATCG-GAAGAGCACACGTCTGAACTCCAGTCAC 3' (SEQ ID NO: 6); 5' GTCATAGCTAGAGTACAGATCG-GAAGAGCACACGTCTGAACTCCAGTCAC 3' (SEQ ID NO: 8); 5' GTCAACGAGTGCTCTGAGATCG-GAAGAGCACACGTCTGAACTCCAGTCAC 3' (SEQ ID NO: 10); 5' GTCAGACTATCGCATGAGATCG-GAAGAGCACACGTCTGAACTCCAGTCAC 3' (SEQ ID NO: 12); 5' GTCACTCGACTGATGAAGATCG-GAAGAGCACACGTCTGAACTCCAGTCAC 3' (SEQ ID NO: 14); 5' GTCAATACCGCTGATTAGATCG-GAAGAGCACACGTCTGAACTCCAGTCAC 3' (SEQ ID NO: 16); 5' GTCACAGTAGTATGCTAGATCG-GAAGAGCACACGTCTGAACTCCAGTCAC 3' (SEQ ID NO: 18); 5' GTCAACGTGTATCAGCAGATCG-GAAGAGCACACGTCTGAACTCCAGTCAC 3' (SEQ ID NO: 20); 5' GTCACGTGTGACAGAGAGATCG-GAAGAGCACACGTCTGAACTCCAGTCAC 3' (SEQ ID NO: 22); 5' GTCATGATGACGTAGCAGATCG-GAAGAGCACACGTCTGAACTCCAGTCAC 3' (SEQ ID NO: 24); 5' GTCAAGTGACATCTGCAGATCG-GAAGAGCACACGTCTGAACTCCAGTCAC 3' (SEQ ID NO: 26); 5' GTCACTAGCTGTGAGTAGATCG-GAAGAGCACACGTCTGAACTCCAGTCAC 3' (SEQ ID NO: 28); 5' GTCATACATGAGCGAGAGATCG-GAAGAGCACACGTCTGAACTCCAGTCAC 3' (SEQ ID NO: 30); 5' GTCACTAGTGCAGCTAAGATCG-GAAGAGCACACGTCTGAACTCCAGTCAC 3' (SEQ ID NO: 32); 5' GTCATAGCTCGAACTGAGATCG-GAAGAGCACACGTCTGAACTCCAGTCAC 3' (SEQ ID NO: 34); 5' GTCAGCGAGTCATGCAAGATCG-GAAGAGCACACGTCTGAACTCCAGTCAC 3' (SEQ ID NO: 36); 5' GTCATGTACAGTACACAGATCG-GAAGAGCACACGTCTGAACTCCAGTCAC 3' (SEQ ID NO: 38); 5' GTCATCAGACTCTAGTAGATCG-GAAGAGCACACGTCTGAACTCCAGTCAC 3' (SEQ ID NO: 40); 5' GTCAGACACGCACTCTAGATCG-GAAGAGCACACGTCTGAACTCCAGTCAC 3' (SEQ ID NO: 42); 5' GTCAATCTGATGCGTAAGATCG-GAAGAGCACACGTCTGAACTCCAGTCAC 3' (SEQ ID NO: 44); 5' GTCAACTGTCATGCAGAGATCG-GAAGAGCACACGTCTGAACTCCAGTCAC 3' (SEQ ID NO: 46); and 5' GTCAGTGAGATCGTACAGATCG-GAAGAGCACACGTCTGAACTCCAGTCAC 3' (SEQ ID NO: 48).

In certain embodiments of the nucleic acid adapters, the 5' end of the first oligonucleotide strand is labelled with an affinity tag (e.g., biotin). In other embodiments of the nucleic acid adapters, the 3' end of the second oligonucleotide strand is labelled with an affinity tag (e.g., biotin). The nucleic acid adapters of the present technology may be used to sequence a double-stranded target nucleic acid molecule selected from the group consisting of double-stranded DNA or double-stranded RNA. The double-stranded DNA may be sheared genomic DNA, or cell-free DNA.

Additionally or alternatively, in some embodiments, the nucleic acid adapters of the present technology further comprise a sample-specific barcode sequence (e.g., patient barcode), wherein the sample-specific barcode sequence comprises about 2-20 nucleotides. The patient barcode may contain, naturally occurring bases (e.g., Adenosine (A), Thymidine (T), Guanosine (G), Cytosine (C), and Uracil (U)) or non-naturally occurring bases (e.g., aminoallyl-uridine, iso-cytosines, isoguanine, and 2-aminopurine).

In some embodiments, the patient barcode is located at the 5' strand of the non-hybridizable portion of the nucleic acid adapters. In other embodiments, the patient barcode is located at the 3' strand of the non-hybridizable portion of the nucleic acid adapters. Alternatively, in certain embodiments, the patient barcode is located in the hybridizable portion of the nucleic acid adapters.

In any of the above embodiments, the nucleic acid adapters of the present technology may further comprise at least two PCR primer binding sites, at least two sequencing primer binding sites, or any combination thereof. In some embodiments, the PCR primer binding sites and/or the sequencing primer binding sites are present in the non-hybridizable portion of the nucleic acid adapters of the present technology. In other embodiments, the PCR primer binding sites and/or the sequencing primer binding sites are present in the hybridizable portion of the nucleic acid adapters of the present technology. In some embodiments, the sequencing primer binding sites comprise at least one sequence selected from the group consisting of P5, P7, P1, A, and Ion Xpress™.

In any of the above embodiments, a nucleic acid adapter of the present technology may comprise the same primer sequences as the other nucleic acid adapters of the present technology. In other embodiments, the primer sequences on one or more nucleic acid adapters of the present technology can be different from the primer sequences on the other nucleic acid adapters disclosed herein.

Detection Methods of the Present Technology

Disclosed herein are methods for the ultrasensitive detection of nucleic acids, e.g., circulating cell-free DNA, for example, circulating cell-free tumor DNA in a sample. The method accurately quantifies nucleic acids, e.g., cell-free tumor DNA derived from tumors. Because tumor-derived DNA levels often parallel clinical responses to diverse therapies, the method may identify actionable mutations. The method may also be used to noninvasively detect and monitor tumors, thus facilitating personalized cancer therapy.

The present disclosure provides methods for detecting cancer-related mutations in circulating tumor nucleic acids with high sensitivity using next-generation sequencing. The method may be applied to cell-free DNA (cfDNA) containing circulating tumor DNA (ctDNA). The method of the present technology optimizes detection of ctDNA from low input samples, thereby facilitating biopsy-free quantification of variants across hundreds of kilobases.

In some embodiments of the method, SNVs and insertions/deletions with a frequency as low as 0.5% can be detected with a cfDNA input of 5-15 ng. In certain embodiments of the method, SNVs and insertions/deletions with a frequency as low as 0.25% can be detected with a cfDNA input of at least 30 ng.

In one aspect, the present disclosure provides a method for detecting at least one mutation in a double-stranded circulating tumor DNA (ctDNA) molecule present in a sample obtained from a patient comprising (a) ligating a plurality of Y-shaped adapters to both ends of the double-stranded ctDNA molecule to form a double-stranded adapter-ctDNA complex, each Y-shaped adapter comprising a first oligonucleotide strand and a second oligonucleotide strand, wherein the sequence of the first oligonucleotide strand and the sequence of the second oligonucleotide strand are selected from the group consisting of SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; and SEQ ID NO: 47 and SEQ ID NO: 48; (b) amplifying both strands of the adapter-ctDNA complex to produce first amplicons and second amplicons, wherein the first amplicons are derived from the first oligonucleotide strand, and the second amplicons are derived from the second oligonucleotide strand; (c) sequencing the first and second amplicons; (d) detecting at least one mutation in the double-stranded ctDNA molecule, when a mutation detected in the first amplicons is consistent with a mutation detected in the second amplicons. Adapter-ctDNA complexes are formed by attaching the ctDNA molecule to the hybridizable (double-stranded) portion of the Y-shaped adapters.

In some embodiments of the method, the patient is diagnosed with ovarian cancer, breast cancer, colon cancer, lung cancer, prostate cancer, gastric cancer, pancreatic cancer, cervical cancer, liver cancer, bladder cancer, cancer of the urinary tract, thyroid cancer, renal cancer, carcinoma, melanoma, head and neck cancer, or brain cancer.

In certain embodiments of the method, both of the 3' ends of the double-stranded ctDNA molecule further comprise an "A"-overhang. The methods disclosed herein comprise the step of attaching of one molecule to another molecule, e.g., a polynucleotide adapter onto a different polynucleotide. The attaching may comprise ligating the Y-shaped adapters of the present technology to one or more nucleic acids. In some cases, the enzyme used in the ligation is a DNA ligase, e.g., a T4 DNA ligase, E. coli DNA ligase, mammalian ligase, or any combination thereof. The mammalian ligase may be DNA ligase I, DNA ligase III, or DNA ligase IV. The ligase may also be a thermostable ligase.

In some embodiments, the method further comprises enriching the first amplicons and second amplicons with a plurality of bait sequences, wherein the plurality of bait sequences comprises at least one gene region that corresponds to each of a plurality of cancer-related genes. The plurality of cancer-related genes may comprise ALK, BRAF, EGFR, ERBB2, KIT, KRAS, MET, NRAS, NTRK1, PIK3CA, ROS1, and RET Additionally or alternatively, in some embodiments of the method, the plurality of bait sequences are RNA baits, DNA baits, or a mixture of RNA baits and DNA baits. In certain embodiments, the plurality of bait sequences comprises a 1:1 mixture of RNA baits and DNA baits. In other embodiments, the plurality of bait sequences comprises a mixture of RNA baits and DNA baits having a ratio of 2:1, 1.5:1, 0.75:1 or 0.5:1.

In any of the above embodiments, each Y-shaped adapter further comprises at least two sequencing primer binding sites. Additionally or alternatively, in some embodiments, each Y-shaped adapter further comprises a patient-specific barcode sequence, wherein the patient-specific barcode sequence comprises 2-20 nucleotides. Each Y-shaped adapter of the present technology may be labelled with an affinity tag (e.g., biotin).

In some embodiments of the method, the sample comprises no more than 5 ng of cell-free DNA. In other embodiments, the sample comprises at least 6-20 ng of cell-free DNA. In certain embodiments, the sample is whole blood, serum, plasma, synovial fluid, lymphatic fluid, ascites fluid, or interstitial fluid.

Detection may include determining whether the first and the second amplicons originate from the same strand of a double-stranded ctDNA molecule present in the sample by means of identifying the molecular identifier sequences present in the hybridizable portion of the first and second oligonucleotide strands of the Y-shaped adapter of the present technology (i.e., the "double-stranded barcode sequence"). The unique double-stranded barcode sequences can identify strands of the target nucleic acid (e.g., a ctDNA molecule). For example, after an adapter is attached to a target nucleic acid, both strands of the resulting nucleic acid contain the unique double-stranded barcode. After amplification, the amplicons derived from one strand of the nucleic acid contain the same double-stranded barcode as the amplicons derived from the other strand of the same nucleic acid.

Thus, in some embodiments, the double-stranded barcode can be used to identify amplicons derived from the two strands of the same template nucleic acid. In certain embodiments, the unique double-stranded barcodes can be used to identify mutations on one strand, but not the other strand, of the nucleic acid. In certain embodiments, mutations that occur on one strand, but not the other strand, of the template nucleic acid can be amplification errors that can be disregarded as artifacts.

The double-stranded barcode sequence can be located several base pairs away from the base pair which attaches the Y-shaped adapter to the ctDNA molecule. If the molecular identifier sequences can be matched as originating from the same adapter, double strand sequencing is possible. The double-stranded barcode sequence is matched by Watson-Crick pairing.

In the context of the present technology, amplicons derived from the same template nucleic acid shall contain the same unique molecular identifier sequence (UID). These distinct unique molecular identifiers can be used to identify and count the distinct template nucleic acids in the original sample. For example, UIDs can be used to count original template nucleic acids containing the same mutations. In other cases, UIDs can be used to identify and group the amplicons from the same original template nucleic acid.

Samples

Samples may be collected from subjects repeatedly over a period of time (e.g., once a day, once a week, once a month, biannually or annually). Obtaining numerous samples from a subject over a period of time can be used to verify results from earlier detections or to identify an alteration as a result of, for example, drug treatment.

The sample may comprise nucleic acids including tumor nucleic acids. The nucleic acids may be genomic nucleic acids. The nucleic acids may also be circulating nucleic acids, e.g., cell-free nucleic acids. For example, the circulating nucleic acids may be from a tumor, e.g., ctDNA. Sample nucleic acids useful for the methods of the present technology may comprise cfDNAs, e.g., DNA in a sample that is not contained within a cell. Such DNA may be fragmented, e.g., may be on average about 170 nucleotides in length, which may coincide with the length of DNA wrapped around a single nucleosome.

cfDNA may be a heterogeneous mixture of DNA from normal and tumor cells, and an initial sample of cfDNA may not be enriched for cancer cell DNA and recurrently mutated regions of a cancer cell genome. One of skill in the art will understand that non-mutated germline sequences may not be distinguished between a tumor source and a normal cell source, but sequences containing somatic mutations have a probability of being derived from tumor DNA. In some embodiments, a sample may comprise control germline DNAs. A sample may also comprise known tumor DNAs. Further, a sample may comprise cfDNAs obtained from an individual suspected of having ctDNA in the sample. Additionally, a sample may comprise cfDNAs obtained from an individual not suspected of having ctDNA in the sample, for example, as part of routine testing.

The methods disclosed herein may comprise obtaining one or more samples, e.g., nucleic acid samples, from a subject. The one or more sample nucleic acids may be tumor nucleic acids. For example, nucleic acids may be extracted from tumor biopsies. Tumor nucleic acids may also be released into the blood stream from tumor cells, e.g., as a result of immunological responses to the tumor. The tumor nucleic acid that is released into the blood can be ctDNA.

The one or more sample nucleic acids may be genomic nucleic acids. It should be understood that the step of obtaining tumor nucleic acids and genomic nucleic acids from a subject with a specific cancer may occur simultaneously. For example, venipuncture to collect blood, plasma, or serum, may simultaneously collect both genomic and tumor nucleic acids. Obtaining tumor nucleic acids and genomic nucleic acids from a subject with a specific cancer may also occur at separate occasions. For example, it may be possible to obtain a single tissue sample from a patient, for example, a biopsy sample, which includes both tumor nucleic acids and genomic nucleic acids. It is also possible to obtain the tumor nucleic acids and genomic nucleic acids from the subject in separate samples, in separate tissues, or at separate times.

Obtaining tumor nucleic acids and genomic nucleic acids from a subject with a specific cancer may also include the process of extracting a biological fluid or tissue sample from the subject with the specific cancer. Obtaining the nucleic acids may include procedures to improve the yield or recovery of the nucleic acids, such as separating the nucleic acids from other cellular components and contaminants that may be present in the biological fluid or tissue sample, e.g., by phenol chloroform extraction, precipitation by organic solvents, or DNA-binding spin columns.

Sometimes, the nucleic acids are mixed or impure. In some embodiments, two or more samples may be isolated from two or more subjects. Patient barcode sequences may be employed to identify a sample from which the nucleic acid originated and to sort the nucleic acids into different groups. In some embodiments, nucleic acids from a first sample may be associated with a first patient barcode, whereas nucleic acids from a second sample may be associated with a second patient barcode.

In other embodiments, the two or more samples may be from the same subject. In certain embodiments, the two or more samples may be from different tissues of the same subjects. For example, one sample may be from a tumor (e.g., a solid tumor) and another sample may be from the blood of the same subject. The samples may be obtained at the same time or at two or more time points.

Amplification

The nucleic acids being amplified can be DNAs, including genomic DNAs, cDNAs (complementary DNA), cell-free DNAs (cfDNAs) and circulating tumor DNAs (ctDNAs). The nucleic acids being amplified can also be RNAs. As used herein, one amplification reaction may consist of many rounds of DNA synthesis.

The methods disclosed herein may comprise amplification of the template nucleic acids comprising sample nucleic acids attached to Y-shaped adapters. Any known techniques for nucleic acid (e.g., DNA and RNA) amplification can be used with the assays described herein. Some amplification techniques are the polymerase chain reaction (PCR) methodologies which can include, but are not limited to, solution PCR and in situ PCR. Alternatively, amplification may comprise non-exponential amplification, such as linear amplification.

Amplification of the template nucleic acids may comprise using bead amplification followed by fiber optics detection as described in U.S. Applications Pub. Nos. 2002/0012930, 2003/0058629, 2003/0100102, 2003/0148344, 2004/0248161, 2005/0079510, 2005/0124022, and 2006/0078909.

Amplification of the template nucleic acid may comprise the use of one or more polymerases. The polymerase may be a DNA polymerase or an RNA polymerase. In some embodiments, the polymerase may be a high fidelity polymerase, KAPA HiFi DNA polymerase. The polymerase may also be Phusion DNA polymerase.

In some embodiments, a single primer or one or both primers of a primer pair comprise a specific sequencing adapter ligated to the 5' end of the target specific sequence portion of the primer. This sequencing adapter is a short oligonucleotide of known sequence that can provide a priming site for both amplification and sequencing of the adjoining, target nucleic acid. As such, sequencing adapters allow binding of a fragment to a flow cell for next generation sequencing. Any sequencing adapter may be included within a primer used in the present disclosure.

In some embodiments, all forward amplicons (i.e., amplicons extended from forward primers that hybridized with antisense strands of a target nucleic acid) contain the same sequencing adapter. In some embodiments when double stranded sequencing is performed, all forward amplicons contain the same sequencing adapter and all reverse amplicons (i.e., amplicons extended from reverse primers that hybridized with sense strands of a target segment) contain a sequencing adapter that is different from the sequencing adapter of the forward amplicons.

In some embodiments, the sequencing adapters are P5 and/or P7 adapter sequences that are recommended for Illumina sequencers (MiSeq and HiSeq). See, e.g., Williams-Carrier et al., *Plant J.*, 63(1):167-77 (2010). In some embodiments, the sequencing adapters are P1, A, or Ion Xpress™ barcode adapter sequences that are recommended for Life Technologies sequencers. Other sequencing adapters are known in the art.

Additionally or alternatively, in some embodiments of the above methods, amplicons from more than one sample are sequenced. In some embodiments, all samples are sequenced simultaneously in parallel. In some embodiments of the above methods, amplicons from at least 1, 5, 10, 20, 30, or up to 35, 40, 45, 48 or 50 different samples are amplified and sequenced using the methods described herein.

Additionally or alternatively, in some embodiments of the method, amplicons derived from a single sample may further comprise an identical index sequence that indicates the source from which the amplicon is generated, the index sequence for each sample being different from the index sequences from all other samples. As such, the use of index sequences permits multiple samples to be pooled per sequencing run and the sample source subsequently ascertained based on the index sequence. In some embodiments, the Access Array™ System (Fluidigm Corp., San Francisco, Calif.) or the Apollo 324 System (Wafergen Biosystems, Fremont, Calif.) is used to generate a barcoded (indexed) amplicon library by simultaneously amplifying the nucleic acids from the samples in one set up.

In some embodiments, indexed amplicons are generated using primers (for example, forward primers and/or reverse primers) containing the index sequence. Such indexed primers may be included during library preparation as a "barcoding" tool to identify specific amplicons as originating from a particular sample source. When sequencing adapter-ligated and/or indexed primers are employed, the sequencing adapter and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources. In some embodiments, the amplicon library is generated using a multiplexed PCR approach.

Indexed amplicons from more than one sample source are quantified individually and then pooled prior to high throughput sequencing. As such, the use of index sequences permits multiple samples (i.e., samples from more than one sample source) to be pooled per sequencing run and the sample source subsequently ascertained based on the index sequence. When indexed primer sets are used, this capability can be exploited for comparative studies. In some embodiments, amplicon libraries from up to 48 separate sources are pooled prior to sequencing.

End Repair

The methods disclosed herein may comprise performing an end repair reaction on a plurality of target nucleic acids (e.g., cfDNA) to produce a plurality of end repaired nucleic acids. For example, the end repair reaction may be conducted prior to attaching the Y-shaped adapters of the present technology to the plurality of target nucleic acids.

In some embodiments, the end repair reaction may be conducted prior to amplification of the adapter-modified nucleic acids. In other embodiments, the end repair reaction may be conducted after amplification of the adapter-modified nucleic acids.

In some embodiments, the end repair reaction may be conducted prior to fragmenting the plurality of target nucleic acids. In other embodiments, the end repair reaction may be conducted after fragmenting the plurality of target nucleic acids.

The end repair reaction may also be performed by using one or more end repair enzymes. In some embodiments, enzymes for repairing DNA can comprise polymerase and exonuclease. For example, polymerase can fill in the missing bases for a DNA strand from 5' to 3' direction. The resulting double-stranded DNA can be the same length as the original longest DNA strand. Exonuclease can remove the 3' overhangs. The resulting double-stranded DNA can be the same length as the original shortest DNA strand.

A-Tailing

The methods disclosed herein may comprise performing an A-tailing reaction on the plurality of target nucleic acids (e.g., cfDNA) to produce a plurality of A-tailed nucleic acids. For example, the A-tailing reaction may be conducted prior to attaching the Y-shaped adapters of the present technology to the plurality of nucleic acids.

Further, the A-tailing reaction may be conducted prior to amplification of the adapter-modified nucleic acids. In other embodiments, the A-tailing reaction may be conducted after amplification of the adapter-modified nucleic acids.

In some embodiments, the A-tailing reaction may be conducted prior to fragmenting the plurality of target nucleic acids. In some cases, the A-tailing reaction may be conducted after fragmenting the plurality of target nucleic acids.

In other embodiments, the A-tailing reaction may be conducted prior to end repair of the plurality of target nucleic acids. In some embodiments, the A-tailing reaction may be conducted after end repair of the plurality of target nucleic acids.

The A-tailing reaction may also be performed by using one or more A-tailing enzymes. For example, an A residue can be added by incubating a DNA fragment with dATP and a non-proofreading DNA polymerase, which will add a single 3' "A" residue.

NGS Platforms

Genotyping, detection, identification or quantitation of the ctDNA can utilize sequencing. Sequencing can be accomplished using high-throughput massively parallel sequencing. Sequencing can be performed using nucleic acids described herein such as genomic DNA, cfDNA, cDNA derived from RNA transcripts or RNA as a template. For example, sequence information of the cell-free DNA sample may be obtained by massively parallel sequencing. In some embodiments, massively parallel sequencing may be performed on a subset of a genome, e.g., from a subset of cfDNA from the cfDNA sample. Sequence information can be obtained by parallel sequencing using flow cells. For example, primers for amplification can be covalently attached to slides in the flow cells and then the flow cells can be exposed to reagents for nucleic acids extension and sequencing.

Following the production of an adapter tagged amplicon library, the amplicons are sequenced using high throughput, massively parallel sequencing (i.e., next generation sequencing). In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, Calif.) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454™ GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos Biosciences Corp's (Cambridge, Mass.) single-molecule sequencing uses DNA fragments with added polyA tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA, HiSeq 2500, HiSeq 1500, HiSeq 2000, or HiSeq 1000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)-small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

High-throughput sequencing of RNA or DNA can also take place using AnyDot-chips (Genovoxx, Germany), which allows monitoring of biological processes (e.g., miRNA expression or allele variability (SNP detection)). For example, the AnyDot-chips allow for 10×-50× enhancement of nucleotide fluorescence signal detection. Other high-throughput sequencing systems include those disclosed in Venter, J., et al., *Science* 16 Feb. 2001; Adams, M. et al., *Science* 24 Mar. 2000; and M. J, Levene, et al., *Science* 299:682-686, January 2003; as well as U.S. Application Pub. No. 2003/0044781 and 2006/0078937.

Double Stranded Sequencing

The methods disclosed herein may comprise a step of pairing sequencing reads to obtain a double-stranded (duplex) sequence. The step involves reading each nucleic acid sequence to determine its barcode. In some embodiments, the barcodes on the two strands are complementary to each other (e.g., if the unique molecular IDs are located in the hybridizable portion of the Y-shaped adapter). Under this scenario, Y-shaped adapter tagged nucleic acids are grouped into families sharing the same unique molecular ID (UID) and a consensus sequence is established for each of the two strands to form 'single-strand consensus sequences' (SS-CSs). The two complementary consensus sequences derived from the two strands of an individual DNA duplex are then compared with each other, and the base identity at each position is retained only if the two strands match perfectly at that position, yielding a 'duplex consensus sequence' (DCS).

In some embodiments, the methods disclosed herein comprises a step of error suppressing using barcodes. The method comprises a step of mapping the sequence to the reference genome and identifying all single nucleotide variants (SNVs) (i.e., bases different from the reference sequence). The method further comprises a step of subjecting the SNVs to quality filtering. In some embodiments, the quality filtering is Phred quality filtering using a threshold Q of 30, which eliminates 99.9% of errors arising from sequencing artifacts.

In some embodiments, the method further comprises a step of reducing errors by counting the number of SNVs for each genomic position (subjected to and having passed the quality filtering in the preceding step) and selecting the most abundant variant. In a further embodiment, the method further comprises a step of subtracting sequences with SNVs that have not passed the quality filtering from the group of sequences defined as a barcode family sharing the same UID. The method further comprises a step of consolidating all members of the barcode family into a single sequence, only keeping variants that pass the preceding step with >2 members.

Further, in some embodiments of the method, all non-reference variants in singleton barcode families (i.e., families with one sequence) are eliminated unless supported by evidence from at least one other DNA molecule with >2 family members supporting that variant.

Reducing Background Error

The methods provided herein may further comprise methods of reducing background error. Background errors may comprise mutations that do not occur in vivo but are artificially generated, e.g., during amplification or sequencing. Background error mutations, for example, single nucleotide changes, e.g., guanine to thymine (G to T) mutations, may be caused by errors of PCR or sequencing. These mutations occur on one strand of a double-stranded nucleic acid but do not occur on the other strand. These artificial G to T mutations can be detected and disregarded.

Also disclosed herein are methods for reducing background error in sequence of a plurality of amplicons derived from a plurality of nucleic acids, comprising a) identifying mutations from at least a first sequence read and at least a second sequence read, where the mutation from the first sequence read and second sequence read are consistent mutations; b) eliminating mutations that occur on less than 50% of amplicons derived from a single nucleic acid; c) eliminating G to T mutations that occur on first amplicons derived from a first strand of a double-stranded nucleic acid, where the G to T mutations do not occur on second amplicons derived from a second strand of the double-stranded nucleic acid; d) eliminating mutations on amplicons, where a first subset of the amplicons comprises a first double-stranded barcode and a second subset of the amplicons comprise a second double-stranded barcode, where the first double-stranded barcode is different from the second double-stranded barcode; or f) any combination thereof. The term "eliminating" as used herein can refer to disregarding mutation data from the sequence information.

Reducing background error can comprise identifying mutations from at least a first sequence read and at least a second sequence read, wherein the mutation from the first sequence read and second sequence read are consistent mutations. In this case, the mutation is a real mutation, e.g., not background error.

In some embodiments, a mutation of a nucleotide identified from a first sequence read of one strand of a double-stranded nucleic acid is consistent with a mutation of the nucleotide identified from a second sequence read of the same strand of the double-stranded nucleic acid. For example, if the mutations are real, e.g., are not background errors, an A mutation (e.g., a nucleotide mutated to A) identified from a sequence read of one strand of a double-stranded nucleic acid should be consistent with an A mutation (e.g., a nucleotide mutated to A) identified from a second sequence read of the same strand of the double-stranded nucleic acid.

In certain embodiments, a mutation of a nucleotide identified from a first sequence read of one strand of a double-stranded nucleic acid is consistent with a mutation of a complementary nucleotide identified from a second sequence read of the other strand of the double-stranded nucleic acid. For example, if the mutations are real, e.g., are not background errors, an A mutation (e.g., a nucleotide mutated to A) identified from a sequence read of one strand of a double-stranded nucleic acid should be consistent with a T mutation (e.g., a nucleotide mutated to T) identified from a sequence read of the other strand of the double-stranded nucleic acid.

Reducing background error may comprise identifying consistent mutations from 2 or more, e.g. up to 20 or more sequence reads.

Mutations that are considered to be background error in the sequence information can randomly occur on various loci, and thus, may not be present on all the amplicons containing a locus of the mutations. In another embodiment, bioinformatic analysis can be performed to remove the mutations that do not occur on all the amplicons containing the same locus.

Background error may comprise mutations that do not occur on all amplicons derived from a single nucleic acid. For example, reducing background error may comprise eliminating mutations that occur on less than about 50% to less than about 75% or less than about 100% of the amplicons derived from a single nucleic acid or below an experimentally determined cut-off level.

The present technology also provides a method of sequencing ctDNA that comprises a step of reducing background errors by grouping the molecules sharing the same unique molecular ID (UID) into families. This step determines the number of original molecules sequenced (as the number of families sharing a UID) and eliminates errors not shared by all the members of the family. These errors can be introduced by oxidative nucleoside damage, PCR, and other exogenous sources during ex vivo copying or processing of the target molecule. The method of grouping molecules by UID and assessing errors is referred to as "deduping." In some embodiments, the present technology provides a method of assessing cancer by analyzing ctDNA with error suppression using molecular barcoding. In some embodiments, the present technology provides a method of error suppression in genotyping ctDNA from a patient using molecular barcoding.

The sequences can then be "deduped" using UIDs as described herein. Given the typically low cfDNA yields in clinical plasma samples, error rates and barcoding performance can be assessed using all recovered molecules (i.e., regardless of UID copy number or strandedness).

Selector Design

Disclosed herein are methods for analyzing nucleic acids to detect cancer. The methods comprise (a) ligating a plurality of Y-shaped adapters via their double-stranded portions to both ends of a plurality of double-stranded nucleic acids to produce adapter-tagged nucleic acids, wherein each Y-shaped adapter comprises a first oligonucleotide strand and a second oligonucleotide strand, wherein the sequence of the first oligonucleotide strand and the sequence of the second oligonucleotide strand are selected from the group consisting of SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; and SEQ ID NO: 47 and SEQ ID NO: 48; (b) amplifying both strands of the adapter-tagged nucleic acids to produce a plurality of amplicons; (c) hybridizing the amplicons with a selector comprising a set of oligonucleotides that selectively hybridize to genomic regions of all or a subset of the one or more sample nucleic acids; and (d) sequencing the hybridized amplicons to detect presence or absence of cancer or cancer-related mutations. In some embodiments, the double-stranded nucleic acids are genomic DNA, cfDNA, ctDNA, or cDNA derived from RNA transcripts.

Somatic mutations, which are mutations that occur in any of the cells of the body except the germ-line cells, can be characteristic of cancer cells. Most human cancers are relatively heterogeneous for somatic mutations in individual genes. A selector can be used to enrich tumor-derived nucleic acid molecules from total genomic nucleic acids. The design of the selector can dictate which mutations can be detected with high probability for a patient with a given cancer. The selector size can also directly impact the cost and depth of sequence coverage. For example, design and use of selectors are described in part in US 2014/0296081 and Newman et al., Nat Med. 20(5):548-54 (2014), incorporated herein by reference in their entirety.

The methods disclosed herein may comprise one or more selectors or uses of the one or more selectors. A selector may comprise a plurality of oligonucleotides or probes that hybridize with one or more genomic regions. The genomic regions may comprise one or more mutated regions. The genomic regions may comprise one or more mutations associated with one or more cancers.

The plurality of genomic regions may comprise different genomic regions. In some embodiments, the plurality of genomic regions may comprise from a few to up to 7500 different genomic regions.

A genomic region may comprise a protein-coding region, or a portion thereof. A protein-coding region may refer to a region of the genome that encodes a protein, e.g., a gene. A genomic region may comprise two or more genes, protein-coding regions, or portions thereof. A gene may also comprise non-coding sequences, such as an intron, or untranslated region (UTR) or portions thereof. In some embodiments, a genomic region does not comprise an entire gene. A genomic region may comprise a pseudogene, a transposon, or a retrotransposon.

A genomic region may comprise a non-protein-coding region. In some embodiments, a non-protein-coding region may be transcribed into a non-coding RNA (ncRNA). In some embodiments, the non-coding RNA may be a transfer RNA (tRNA), ribosomal RNA (rRNA), regulatory RNA, small nuclear RNA (snRNA), small nucleolar RNA (snoRNA), microRNA, small interfering RNA (siRNAs), Piwi-interacting RNA (piRNA), or long ncRNA.

A genomic region may comprise a recurrently mutated region, e.g., a region of the genome, usually the human genome, in which there is an increased probability of genetic mutation in a cancer of interest, relative to the genome as a whole. A recurrently mutated region may also refer to a region of the genome that comprises one or more mutations that is recurrent in the population. A recurrently mutated region may be characterized by a 'Recurrence Index" (RI).

The RI generally refers to the number of individual subjects (e.g., cancer patients) with a mutation that occurs within a given kilobase of genomic sequence (e.g., number of patients with mutations/genomic region length in kb). A genomic region may also be characterized by the number of patients with a mutation per exon. Thresholds for each metric (e.g., RI and patients per exon or genomic region) may be selected to statistically enrich for known or suspected drivers of the cancer of interest. Thresholds can also be selected by arbitrarily choosing the top percentile for each metric.

The number of genomic regions in a selector may vary depending on the nature of the cancer. The inclusion of larger numbers of genomic regions may generally increase the likelihood that a unique somatic mutation will be identified. For example, the entire genome of a tumor sample and a genomic sample could be sequenced, and the resulting sequences could be compared to note any differences with the non-tumor tissue.

The library of recurrently mutated genomic regions, or "selector" can be used across an entire population for a given cancer, and does not need to be optimized for each subject.

The method may further comprise a hybridization reaction, e.g., hybridizing the amplicons with a selector comprising a set of oligonucleotides that selectively hybridizes to genomic regions of one or more sample nucleic acids. In some embodiments, the hybridization reaction may comprise hybridizing the plurality of amplicons to a solid support, e.g., a plurality of beads.

The method may further comprise conducting a hybridization reaction after an enzymatic reaction. For example, in some embodiments, the enzymatic reaction may comprise one or more of a ligation reaction, a fragmentation reaction, an end repair reaction, an A-tailing reaction, or an amplification reaction.

The selector may also comprise a set of oligonucleotides. The set of oligonucleotides may hybridize to less than 100 kb and up to 1.5 Megabases (Mb) of the genome. The set of oligonucleotides may be capable of hybridizing at least 5 and up to 500 or more different genomic regions. The selector may also hybridize to a range of different genomic regions, e.g., between about 10 to about 1000 different genomic regions. The selector may also hybridize to a plurality of genomic regions, e.g., about 50 to about 7500 different genomic regions.

A selector may hybridize to a genomic region comprising a mutation that is not recurrent in the population. For example, a genomic region may comprise one or more mutations that are present in a given subject. In some embodiments, a genomic region that comprises one or more mutations in a subject may be used to produce a personalized selector for the subject.

The selector may hybridize to a plurality of genomic regions comprising one or more mutations selected from a group consisting of SNV, CNV, insertions, deletions, and rearrangements.

A selector may hybridize to a mutation in a genomic region known or predicted to be associated with a cancer. A mutation in a genomic region known to be associated with a cancer may be referred to as a "known somatic mutation." A known somatic mutation may be a mutation located in one or more genes known to be associated with a cancer and may be a mutation present in one or more oncogenes. For example, known somatic mutations may include one or more mutations located in EGFR, KRAS, or BRAF. Alternatively, a selector may hybridize to a mutation in a genomic region that has not been reported to be associated with a cancer. A genomic region may comprise a sequence of the human genome of sufficient size to capture one or more recurrent mutations.

The methods of the present technology may be directed at cfDNA, which is generally less than about 200 bp in length, and thus a genomic region may be generally less than about 10 kb. Generally the genomic region for a SNV can be quite short, from about 45 bp to about 500 bp in length, while the genomic region for a fusion or other genomic rearrangement may be longer, from about 1 Kb to about 10 Kb in length. A genomic region in a selector may be less than 10 Kb, for example, 100 bp to 10 Kb. In some embodiments, the total sequence covered by the selector is less than about 1.5 megabase pairs (Mb), e.g., 10 kb to 1.5 Mb.

In certain embodiments, a selector useful in the methods of the present technology comprises variants obtained from whole genome sequencing of tumors. For example, the list of variants can be obtained from exome-sequencing nucleic acids from collections of tumor samples, such as a collection of lung squamous cell carcinoma (SCC) tumors or lung adenocarcinoma tumors or any other collections of one or more types of tumors available for sequencing analysis. The sequences may be filtered to eliminate variants located in repeat-rich genomic regions (such as for example, simple repeats, microsatellites, interrupted repeats and segmental duplications). The sequences may also (or instead) be filtered to eliminate variants located in intervals with low mapping rates or low k-mer uniqueness.

Selectors used in the methods disclosed herein can be designed to cover as many patients and mutations per patient as possible with the least amount of genomic space.

In some embodiments, the present disclosure provides a method of creating a selector, i.e., selecting genomic regions to be analyzed in a patient. The selectors may be designed to prioritize inclusion of genomic regions based on the "recurrence index" (RI) metric defined herein. In some embodiments, genomic regions to be included in the selector are exons or smaller portions of an exon containing known lesions. A genomic region to be included comprises the known lesion and is flanked by one or more base pairs to a minimum tile size of 100 bp.

In certain embodiments, genomic regions are ranked by decreasing RI, and those in the highest ranks of both RI and the number of patients per exon are included in the selector. In some embodiments, the highest rank is higher or equal to the top 10%. In this embodiment, the selector has maximized additional patient coverage with minimal space. In some embodiments, the process of selecting genomic regions is repeated under less stringent conditions, i.e., the percentile rank lower than top 10%, e.g., top 33% may be selected. In this embodiment, the method results in including regions that maximally increase the median number of mutations per patient. In some embodiments, inclusion of further genomic regions into a selector is terminated when a predetermined size is reached. In some embodiments, the predetermined desired size is about 100-200 kb. In other embodiments, inclusion of further genomic regions into a selector is terminated when all genomic regions satisfying the filters described above are exhausted.

In some embodiments, the selector comprising genomic regions containing single nucleotide variations (SNVs) further comprises clinically relevant regions containing other types of mutations, e.g., fusions, seed regions, copy number variations (CNVs) and histology classification regions.

The selector can be designed for a specific cancer, for example, non-small cell lung cancer (NSCLC), breast cancer, endometrial uterine carcinoma, etc. The selector can also be designed for a generic class of cancers, e.g., epithelial cancers (carcinomas), sarcomas, lymphomas, melanomas, gliomas, teratomas, etc. The selector can also be designed for a subgenus of cancers, e.g., adenocarcinoma, squamous cell carcinoma, and the like.

The selector may comprise information pertaining to a plurality of genomic regions comprising one or more mutations present in at least one subject suffering from a cancer. For example, the selector may comprise information pertaining to a plurality of genomic regions comprising up to 20 mutations present in at least one subject suffering from a cancer. In some embodiments, the selector may comprise information pertaining to a plurality of genomic regions comprising up to 200 or more mutations present in at least one subject suffering from a cancer. In some embodiments, the one or more mutations within the plurality of genomic regions may be present in at least 1% and up to 20% or more (e.g., up to 95% or more) subjects from a population of subjects suffering from a cancer.

Estimating Tumor Burden

In some embodiments, the present disclosure provides a method of determining tumor burden in a patient by sequencing duplex molecules in the patient's cfDNA.

The methods disclosed herein may comprise a step of designing a selector covering an adequate number (e.g., >1,500) of sequence variations, such as non-synonymous mutations (i.e., a nucleotide mutation that alters the amino acid sequence of a protein). The selector may be designed by any survey method, e.g., exome sequencing of tumors. In some embodiments, a personalized selector may be designed by exome sequencing the patient's tumor. The method further comprises a step of duplex sequencing the patient's cfDNA. In some embodiments, as little as 1,000 genome equivalents may be recoverable in this step.

Treatment Selection Based on ctDNA Screening

Disclosed herein are methods for determining whether a patient harboring one or more ctDNA mutations will benefit from treatment with at least one therapeutic agent.

In one aspect, the present disclosure provides a method for selecting a patient for treatment with at least one therapeutic agent comprising: (a) ligating a plurality of Y-shaped adapters to both ends of a double-stranded ctDNA molecule present in a sample obtained from the patient to form a double-stranded adapter-ctDNA complex, each Y-shaped adapter comprising a first oligonucleotide strand and a second oligonucleotide strand, wherein the sequence of the first oligonucleotide strand and the sequence of the second oligonucleotide strand are selected from the group consisting of SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; and SEQ ID NO: 47 and SEQ ID NO: 48; (b) amplifying both strands of the adapter-ctDNA complex to produce first amplicons and second amplicons, wherein the first amplicons are derived from the first oligonucleotide strand, and the second amplicons are derived from the second oligonucleotide strand; (c) sequencing the first and second amplicons; (d) detecting at least one mutation in the double-stranded ctDNA molecule, when a mutation detected in the first amplicons is consistent with a mutation detected in the second amplicons; and (e) selecting the patient for treatment with at least one therapeutic agent if a mutation is detected in the double-stranded ctDNA molecule, wherein the ctDNA molecule corresponds to ALK, BRAF, EGFR, ERBB2, KIT, KRAS, MET, NRAS, NTRK1, PIK3CA, ROS1, or RET In some embodiments, the at least one therapeutic agent comprises one or more of anti-HER-2 therapies, anti-EGFR tyrosine kinase inhibitors, PI3K/AKT/mTor pathway inhibitors, kinase inhibitors, BRAF inhibitors, ALK/MET inhibitors, ERBB2 antagonists, and RAF/MEK/ERK inhibitors.

In certain embodiments, the EGFR tyrosine kinase inhibitor is gefitinib or erlotinib. In certain embodiments, the anti-EGFR therapy is cetuximab.

In some embodiments of the method, the anti-HER-2 therapy is trastuzumab or lapatinib.

Examples of kinase inhibitors include but are not limited to crizotinib, afatinib, Axitinib, bevacizumab, Bosutinib, Cetuximab, Dasatinib, Erlotinib, Fostamatinib, Gefitinib, Imatinib, Lapatinib, Lenvatinib, Nilotinib, Panitumumab, Pazopanib, Pegaptanib, Ranibizumab, Ruxolitinib, Sorafenib, Sunitinib, Trastuzumab, and Vemurafenib.

Examples of BRAF inhibitors include, but are not limited to GDC-0879, SB590885, Encorafenib, RAF265, TAK-632, PLX4720, CEP-32496, AZ628, Sorafenib Tosylate, Sorafenib, Vemurafenib (Zelboraf) and Dabrafenib (GSK2118436).

Examples of RAF/MEK/ERK inhibitors include, but are not limited to Vemurafenib (Zelboraf) and Dabrafenib (GSK2118436), Encorafenib, TAK-632, PLX4720, MLN2480, Cobimetinib (GDC-0973), MEK 162, RO5126766, GDC-0623, VTX11e, Selumetinib (AZD6244), PD0325901, Trametinib (GSK1120212), U0126-EtOH, PD184352 (CI-1040), Refametinib, PD98059, BIX02189, Binimetinib, Pimasertib (AS-703026), SL327, BIX02188, AZD8330, TAK-733, PD318088, SCH772984, and FR 180204.

Examples of PI3K/AKT/mTor pathway inhibitors include, but are not limited to BKM120, BEZ235, Pictilisib (GDC-0941), LY294002, CAL-101 (Idelalisib), GNE-317, PI-3065, HS-173, PI-103, NU7441, GSK2636771, VS-5584, CZC24832, Duvelisib, TG100-115, A66, YM201636, CAY10505, GSK1059615, PF-04691502, PIK-75, PIK-93, AS-605240, BGT226, AZD6482, Voxtalisib, Alpelisib, CUDC-907, IC-87114, Omipalisib, TG100713, Gedatolisib, CH5132799, PKI-402, BAY 80-6946, TGX-221, XL147, PIK-90, PIK-293, PIK-294, 3-Methyladenine, Quercetin, Wortmannin, ZSTK474, AS-252424, AS-604850, everolimus, and Apitolisib.

Examples of ERBB2 antagonists include, but are not limited to Lapatinib, Canertinib, CP-724,714, AZD8931, AEE788, Tyrphostin AG 879, Mubritinib, and Pertuzumab.

Examples of ALK inhibitors include, but are not limited to Crizotinib, TAE684, Alectinib, Ceritinib, AP26113, AZD3463, and ASP3026.

Examples of MET inhibitors include, but are not limited to Crizotinib, PHA-665752, SU11274, SGX-523, BMS-777607, JNJ-38877605, Tivantinib, PF-04217903, MGCD-265, Capmatinib, AMG 208, MK-2461, AMG 458, NVP-BVU972, and Tepotinib.

The methods of the present technology are useful in assessing the efficacy of a cancer therapeutic regimen in a patient. ctDNA expression levels/ctDNA expression profiles provide conveniently measurable benchmarks by which to gauge the effectiveness of a cancer therapeutic regimen.

In one aspect, the present disclosure provides a method for evaluating the efficacy of a therapeutic regimen in a subject diagnosed with, or suspected of having cancer comprising (a) detecting ctDNA mutations in a test sample obtained from the subject during or after administration of the therapeutic regimen using the nucleic acid adapters and methods disclosed herein, and (b) determining the efficacy of the therapeutic regimen by detecting alterations in the ctDNA expression levels and/or ctDNA expression profile present in the test sample relative to that observed in a reference sample obtained from the subject prior to administration of the therapeutic regimen. In some embodiments of the method, the therapeutic regimen is determined to be efficacious if the ctDNA expression levels present in the test sample are decreased relative to that observed in a reference sample obtained from the subject prior to administration of the therapeutic regimen. In some embodiments of the method, the therapeutic regimen is determined to be efficacious if the ctDNA expression profile present in the test sample is comparable to that observed in a reference sample obtained from a normal (cancer-free) control subject.

In some embodiments, the therapeutic regimen is selected based on the ctDNA expression levels and/or ctDNA expression profile observed in the subject prior to administration of the therapeutic regimen. The therapeutic regimen may be maintained, discontinued, or subsequently modified based on the ctDNA expression levels and/or ctDNA expression profile observed in the subject during or after the administration of the therapeutic regimen.

In another aspect, the methods described herein are useful in identifying patient populations that exhibit different degrees of sensitivities to a therapeutic agent (e.g., a therapeutic agent disclosed herein or an anti-cancer therapeutic agent known in the art). Age, gender, height, weight, ethnicity, family history of genetic disorders, immunocompromised status, and medical history are non-limiting examples of factors that can impact responsiveness of a patient to a particular therapeutic agent.

Alterations in ctDNA expression levels and/or ctDNA expression profiles can be used to classify patients based on their responsiveness to a specific dose of a therapeutic agent. In some embodiments, a patient may be responsive, non-responsive, or hyper-responsive to a therapeutic agent at a specific dose or a range of doses. Determining patient sensitivity to a therapeutic agent is useful in optimizing therapeutic efficacy and reducing side effects associated with the therapeutic agent. In certain embodiments, the dose of the therapeutic agent may be adjusted to achieve therapeutic efficacy and/or minimize side effects based on alterations in ctDNA expression levels and/or ctDNA expression profiles in treated patients. In other embodiments, a therapeutic agent may be supplemented with an additional therapeutic agent to achieve therapeutic efficacy and/or minimize side effects based on alterations in ctDNA expression levels and/or ctDNA expression profiles in treated patients. In another embodiment, treatment with a therapeutic agent may be temporarily or completely discontinued to achieve therapeutic efficacy and/or minimize side effects based on alterations in ctDNA expression levels and/or ctDNA expression profiles in treated patients.

Kits

The present disclosure also provides kits for detecting alterations in ctDNA or ctDNA in a sample.

Kits of the present technology comprise one or more Y-shaped nucleic acid adapters disclosed herein. In some embodiments, the kits of the present technology further comprise bait sequences that are useful for detecting mutations in various ctDNA or ctDNA sequences that correspond to one or more cancer-related genes including, but not limited to ALK, BRAF, EGFR, ERBB2, KIT, KRAS, MET, NRAS, NTRK1, PIK3CA, ROS1, and RET.

In some embodiments, the kits further comprise buffers, enzymes having polymerase activity, enzymes having polymerase activity and lacking 5'→3' exonuclease activity or both 5'→3' and 3'→5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of alterations in target nucleic acid sequences (e.g., ctDNA).

In one embodiment, the kits of the present technology further comprise a positive control nucleic acid sequence and a negative control nucleic acid sequence to ensure the integrity of the assay during experimental runs. A kit may further contain a means for comparing the ctDNA profile in a sample derived from a cancer patient with a reference nucleic acid sample (e.g., a non-cancerous cfDNA sample). The kit may also comprise instructions for use, software for automated analysis, containers, packages such as packaging intended for commercial sale and the like.

The kits of the present technology can also include other necessary reagents to perform any of the NGS techniques disclosed herein. For example, the kit may further comprise one or more of: sequencing adapters, primers, end repair enzymes, A-tailing enzymes, barcode sequences, reaction tubes, ligases, ligase buffers, wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

The kits of the present technology may include components that are used to prepare nucleic acids from a test sample for the subsequent amplification and/or detection of alterations in cfDNA or ctDNA. Such sample preparation components can be used to produce nucleic acid extracts from tissue samples. The test samples used in the above-described methods will vary based on factors such as the assay format, nature of the detection method, and the specific tissues, cells or extracts used as the test sample to be assayed. Methods of extracting nucleic acids from samples are well known in the art and can be readily adapted to obtain a sample that is compatible with the system utilized. Automated sample preparation systems for extracting nucleic acids from a test sample are commercially available, e.g., Roche Molecular Systems' COBAS AmpliPrep System, Qiagen's BioRobot 9600, and Applied Biosystems' PRISM™ 6700 sample preparation system.

EXAMPLES

Example 1: General Methods and Procedures

Whole blood samples were collected from patients in Cell-Free DNA BCT® tubes (Streck, Omaha, Nebr.), and subsequently centrifuged to separate the plasma, buffy coat and red blood cell portions. cfDNA was extracted from plasma using the DynaMax Cell Free DNA Extraction Kit (Life Technologies, Grand Island, N.Y.) and the Hamilton Microlab Star (Hamilton Bonaduz A.G., Bonaduz, Switzerland) and KingFisher (Thermo Scientific, Waltham, Mass.) according to manufacturer's instructions DNA was quantified using the Qubit dsDNA High Sensitivity kit (Life Technologies, Grand Island, N.Y.) according to manufacturer's instructions. The isolated cfDNA was subjected to end repair and A-tailing using NEBNext Ultra II End Repair Kit (New England BioLabs, Ipswich, Mass.) according to manufacturer's instructions.

YUMIs were generated and utilized according to the procedures described in Kennedy, S. R. et al., *Nat. Protoc.* 9, 2586-2606 (2014), which is incorporated herein by reference. Oligonucleotides corresponding to the sense and antisense strands of the Y-shaped nucleic acids adapters disclosed herein (YAMIs) were annealed individually in a 96 well plate containing 5× adapter hybridization buffer solution (0.5× TE (pH 8.0), 0.025M NaCl) under the following conditions:

| TEMP ° C. | TIME |
|---|---|
| 95 | 5 min |
| 35 | 1 sec |
| 25 | 5 min |

The annealed YAMIs each having their own double-stranded barcode sequence were subsequently pooled. Some YAMIs were biotinylated.

YAMIs and YUMIs were then ligated to both ends of each cfDNA molecule via their hybridizable (double-stranded) portions using NEBNext Ultra II Ligation Kit (New England BioLabs, Ipswich, Mass.) according to the manufacturer's instructions. The concentration of YAMI adapters used per cfDNA sample (5-30 ng input) was approximately 110 nM. The ligated products were purified using Agencourt Ampure XP beads (Beckman Coulter) according to the manufacturer's instructions. The YAMIs also comprised a patient barcode and a universal sequence that can bind to a sequencing primer (e.g., P5 or P7), which were incorporated during AMP1 using MWS21 (5'-CAAGCAGAAGACGGCAT-ACGAGATXXXXXXXXXGTGACTGGAGTTCA-GACGTG TGC-3' (SEQ ID NO: 99)) and P5_R1_F (5'-AATGATACGGCGACCACCGAGATCTACACTCTTTC CCTACACGACGC-3' (SEQ ID NO: 100)) primers under the following PCR conditions:

| 98° C. | 2 mins | |
| 98° C. | 30 s | 6 cycles |

| | |
|---|---|
| 61° C. | 30 s |
| 72° C. | 1 min |
| 72° C. | 5 min |

The resulting adapter-tagged nucleic acids were pooled and subsequently contacted with streptavidin or biotin conjugated baits (SureSelect$^{XT}$ Target Enrichment System, Agilent Technologies, Santa Clara, Calif. and xGen® Lockdown® Probes or Panels, IDT, Coralville, Iowa) according to the manufacturer's instructions, so as to enrich for target regions in ALK, BRAF, EGFR, ERBB2, KIT KRAS, MET, NRAS, NTRK1, PIK3CA, ROS1, and RET These include exonic regions of EGFR, BRAF, MET ERBB2, KRAS, NRAS, PI3KCA, and KIT and intronic regions of ALK (intron 19), ROS1 (introns 31-35), RET (introns 9-11), and NTKR1 (introns 8-11).

| Parameters | DNA Baits (IDT) | RNA Baits (Agilent) |
|---|---|---|
| Length | 60 nt* | 120 nt |
| Tiling Density | 2x max | 5x max |
| Optimal Hybridization Temperature | 65° C. | 65° C. |
| Optimal Hybridization Time | 4 hours | 16-24 hours |
| Optimal Wash Temp | 60-65° C. | 70-72° C. |

*DNA bait length can range from 60-120 base pairs

The enriched adapter-tagged nucleic acids were subsequently amplified by PCR using P5 and P7 primers. Sequence information of the purified adapter-tagged amplicons was then obtained by next generation sequencing using the Illumina NextSeq platform. A total of 6 samples (five patient samples and a single no-template control sample) were pooled in to a single library for sequencing.

The amplicons were grouped into families sharing the same unique molecular ID (UID) and a particular positional start site when mapped to the human genome. A consensus sequence was established for each of the two strands of an individual duplex molecule to form 'single-strand consensus sequences' (SSCSs). Consensus at each position is reached only if more than 70% of family members share the same nucleotide at that position.

Mutations that were real biological variants occurred on the same locus, while false mutations due to background errors occurred randomly on different loci. In addition, mutations due to background errors occurred on a subset of the amplicons derived from the same template nucleic acid. The amplicons derived from the same template nucleic acid were aligned based on the unique identifier and bioinformatic analysis was performed to filter out the mutations due to background errors, e.g., false mutations, which occurred randomly on different loci, or occurred on a subset of the amplicons derived from the same template nucleic acid. The bioinformatics processing steps implemented for these analyses are described in Kennedy, S. R. et al., Nat. Protoc. 9, 2586-2606 (2014).

Figure 2A:
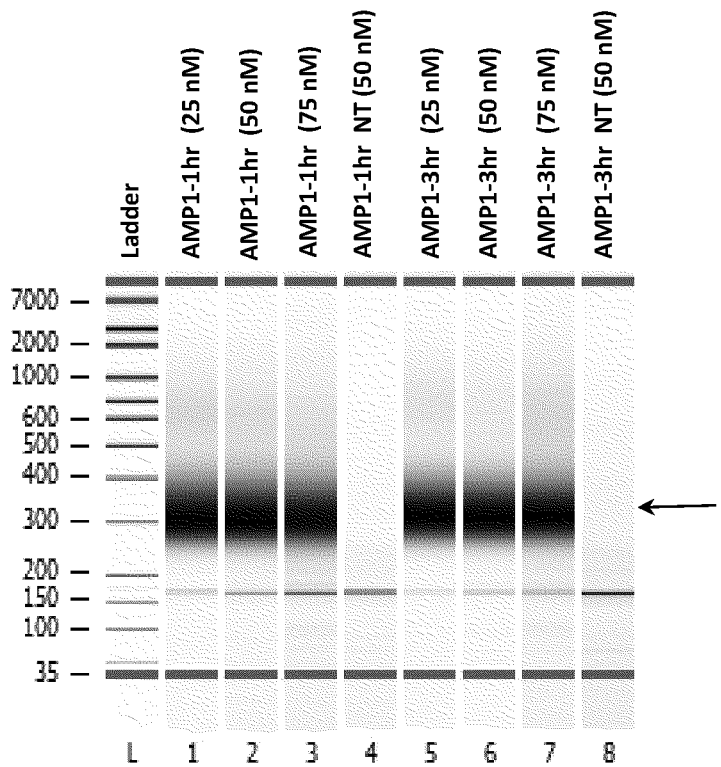
FIG. 2(a) and FIG. 2(b) show the resulting amplicons (corresponding to the arrow in FIG. 2(a) and the ~300 bp peaks in FIG. 2(b)) generated after amplification of the YAMI-ligated DNA library under different experimental conditions. "AMP1" refers to Amplification 1, which is performed after purification of the adapter-ligated molecules to add specimen specific barcodes and to enrich for molecules with correctly ligated adapters.
Figure 2B:
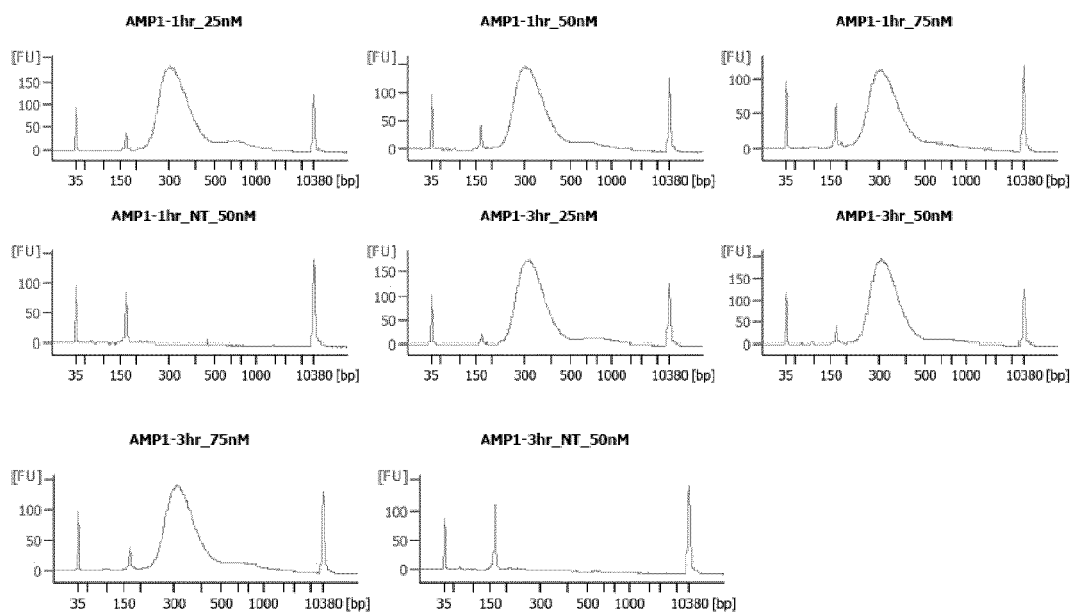

Example 2: Comparative Performance of YAMIs and YUMIs in Detecting Mutations in cfDNA Adapter derived secondary structure formations are known to interfere with the amplification efficiency and enrichment (via hybridization-capture) of correctly ligated target DNA molecules. Ligation experiments with YAMIs revealed that adapter derived secondary structure artifacts (sharp peak at approximately 150 bp) were not amplified during the first round of amplification (AMP1). See FIGS. 2(a) and 2(b). Further, the short YAMIs (shYAMIs) represented by SEQ ID NOS: 1-48 did not form secondary structures during ligation experiments. Moreover, FIGS. 2(a) and 2(b) show that the YAMIs of the present technology were effective in generating cfDNA libraries under different experimental conditions (e.g., YAMI concentrations ranging from 25 nM to 75 nM at a ligation period of 1 hour or 3 hours). Thus, the efficacy of the YAMIs of the present technology can be partly attributed to the absence of adapter derived secondary structure artifacts at the adapter ligation step.

Further, the YAMIs of the present technology were also effective in generating libraries from sheared genomic DNA under different experimental conditions (e.g., YAMI concentrations ranging from 25 nM to 75 nM at a ligation period of 1 hour or 3 hours). See FIG. 3(b).

Figure 6A:
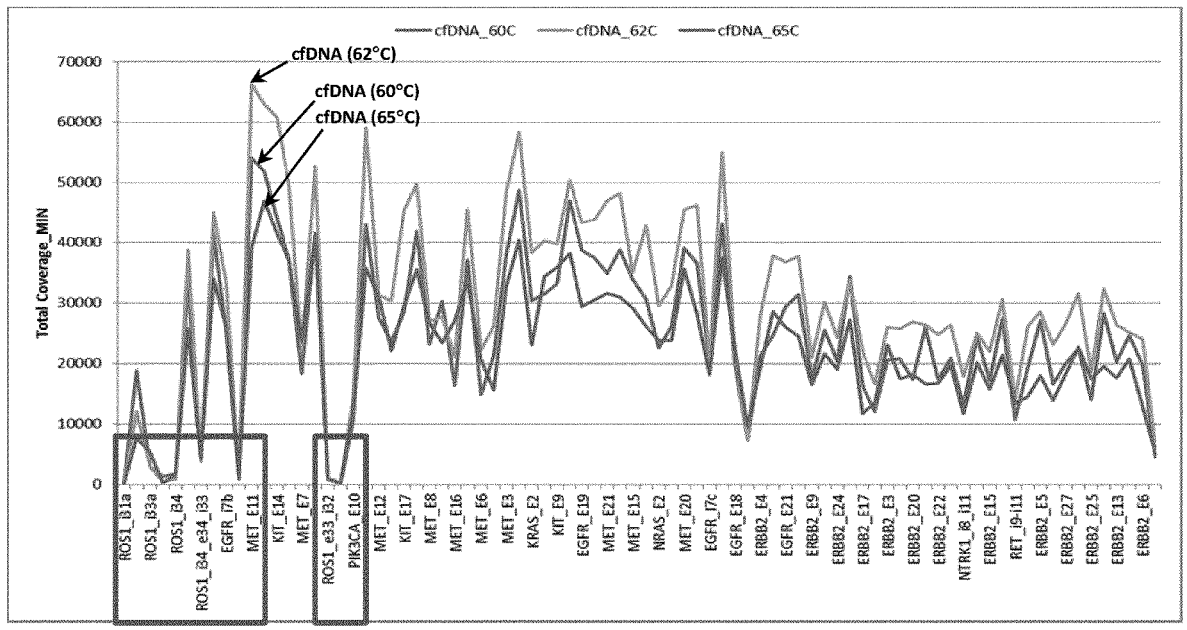
FIG. 6(a) shows the total coverage of the assayed gene regions when enriching amplicons derived from cfDNA with DNA baits under different hybridization and wash conditions. The temperatures recited in FIG. 6(a) refer to both the hybridization and wash temperatures. For example, a 60° C. temperature indicates that the hybridization and wash steps were both performed at 60° C.
Figure 6B:
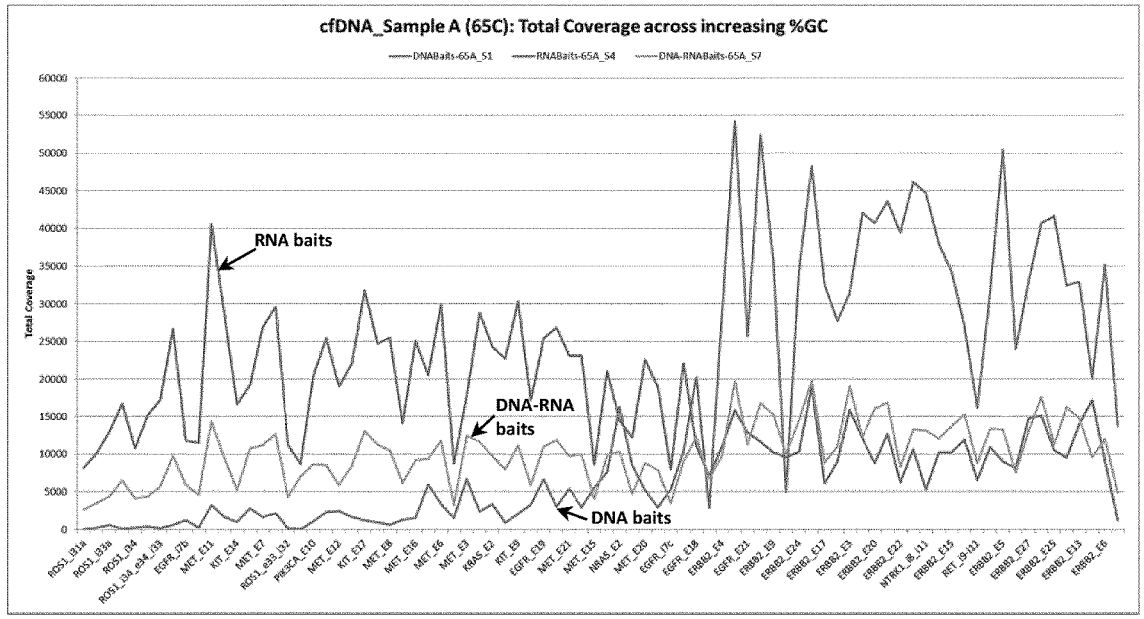
FIG. 6(b) shows the total coverage of the assayed gene regions when enriching amplicons derived from cfDNA with DNA baits, RNA baits, or a combination of DNA and RNA baits at a hybridization temperature of 65° C., and a wash temperature of 65° C.

FIGS. 6(a) and 6(b) show that the total coverage of the assayed gene regions improved when enriching amplicons derived from cfDNA with a combination of DNA and RNA baits compared to that observed with DNA baits alone. As shown in FIG. 6(a), there were significant drop offs in coverage for specific AT-rich regions when enrichment was performed using DNA baits only. Coverage for AT-rich regions was slightly favored when enrichment was performed using RNA baits only, whereas enrichment using a combination of DNA and RNA baits normalized coverage across all regions (both AT-rich and GC-rich regions). FIG. 6(b).

Figure 1B:
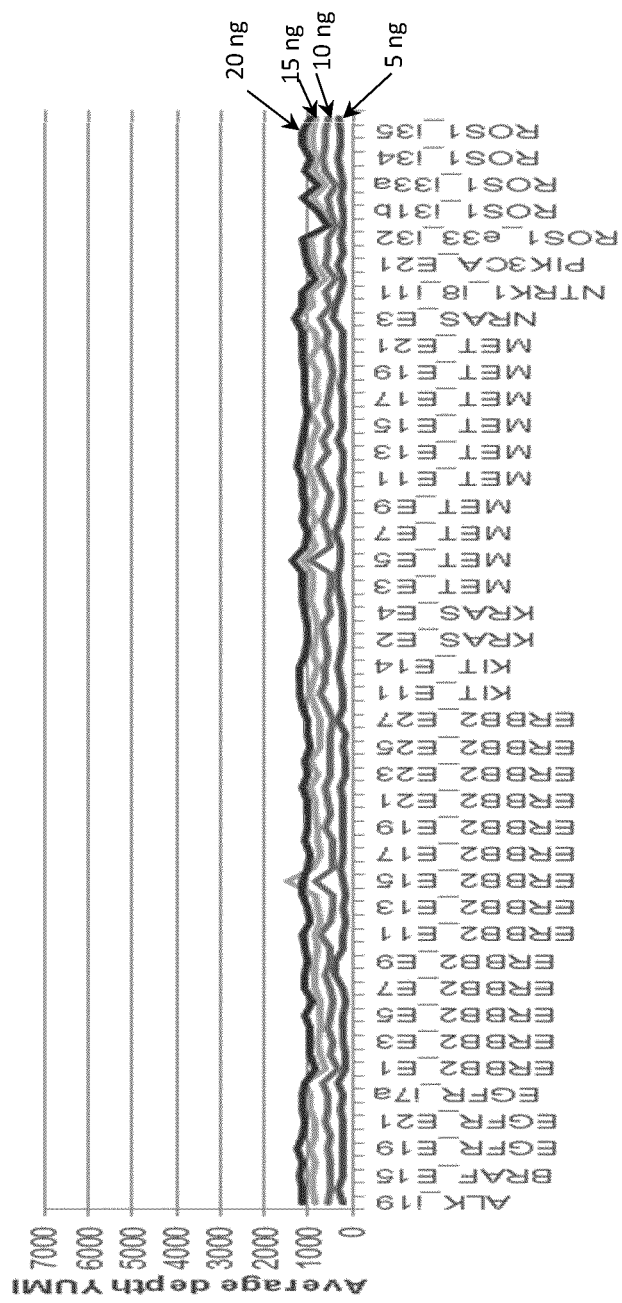
FIG. 1(b) shows the deduped coverage of certain exon or intron regions of several cancer-related genes at varying cfDNA input levels using the adapters described in Kennedy et al. (2014) (hereinafter "YUMIs").
Figure 3A:
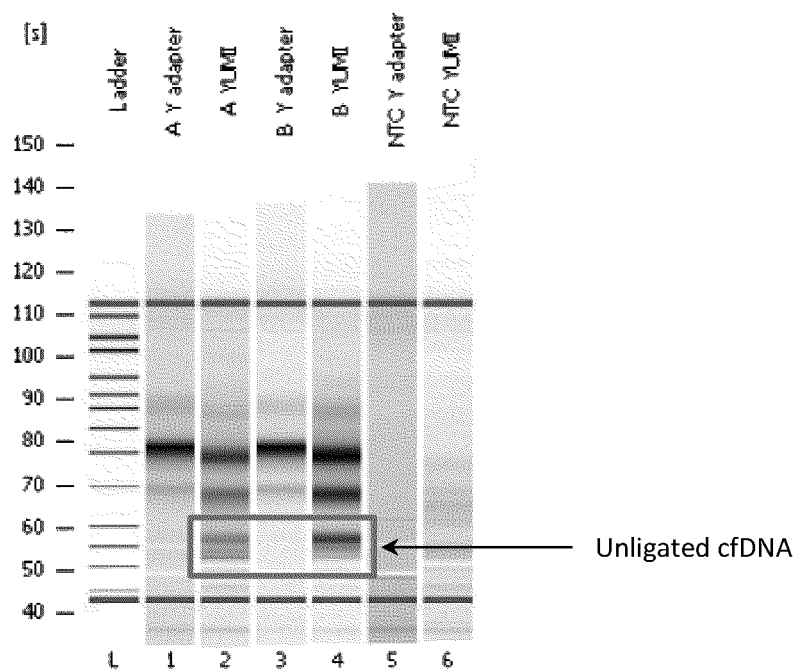
FIG. 3(a) shows the decreased ligation efficiency of YUMIs during DNA library preparation.
Figure 3B:
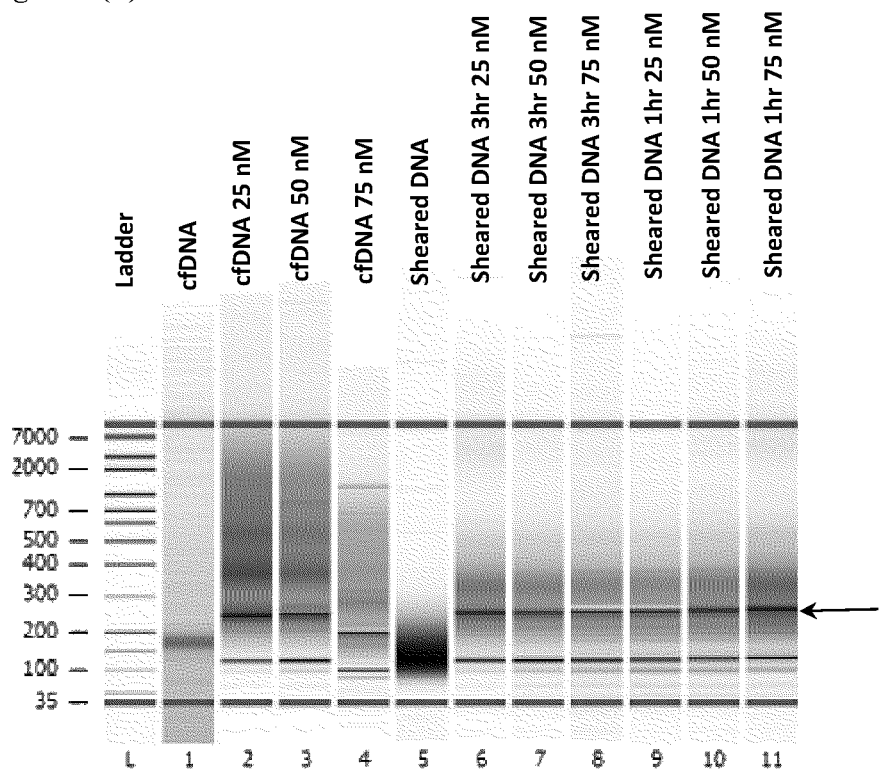
FIG. 3(b) shows the ligation of YAMIs to cfDNA as well as sheared genomic DNA (see arrow) under different experimental conditions.

As shown in FIGS. 1(a) and 1(b), YAMIs showed superior deduped coverage of various regions of many cancer-related genes (e.g., KRAS exon 4, MET exon 13, PIK3CA exon 21, KIT exon 11, BRAF exon 15 and others) at cfDNA input levels of 15 ng compared to that observed with YUMIs. FIG. 1(a) also shows that the deduped coverage of various gene regions obtained with YAMIs was positively correlated with increasing levels of cfDNA input. These results were consistent with the observation that YUMIs showed poor ligation efficiency during cfDNA library preparation relative to that observed with conventional Y-adapters. See FIG. 3(a). As shown in FIG. 3(a), high levels of unligated cfDNA were observed with YUMIs.

YAMIs also showed elevated ligation efficiency during genomic DNA library preparation (input: 15 ng sheared genomic DNA) compared to HPLC or PAGE purified YUMIs. See Table 1.

TABLE 1

| Adapter | unligated | ligated | total | % ligated |
|---|---|---|---|---|
| HPLC_YUMI | 4587.3 | 4774.3 | 9361.6 | 51% |
| PAGE_YUMI | 4646.1 | 5313.8 | 9959.9 | 53% |
| YAMI -peak | 2432.7 | 6072.5 | 8505.2 | 71% |
| YAMI | 2988.5 | 7371.8 | 10360.3 | 71% |

Figure 4:
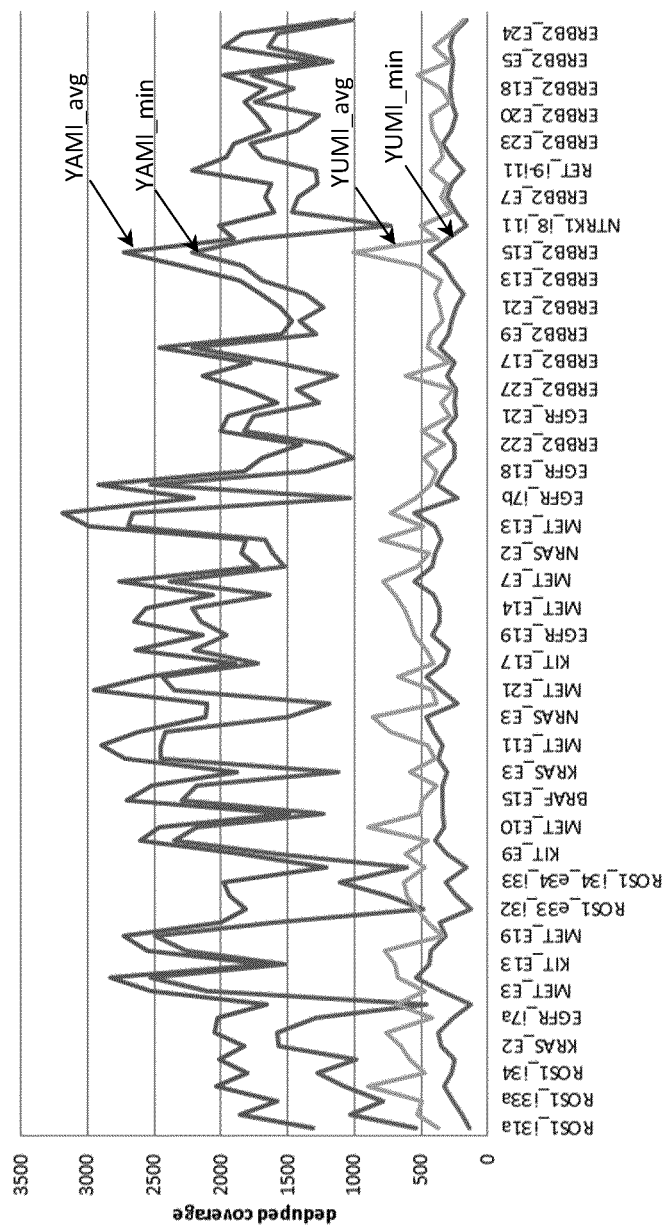
FIG. 4 shows the overall complexity of the cfDNA libraries generated with YAMIs relative to the complexity of cfDNA libraries generated with YUMIs.
Figure 5:
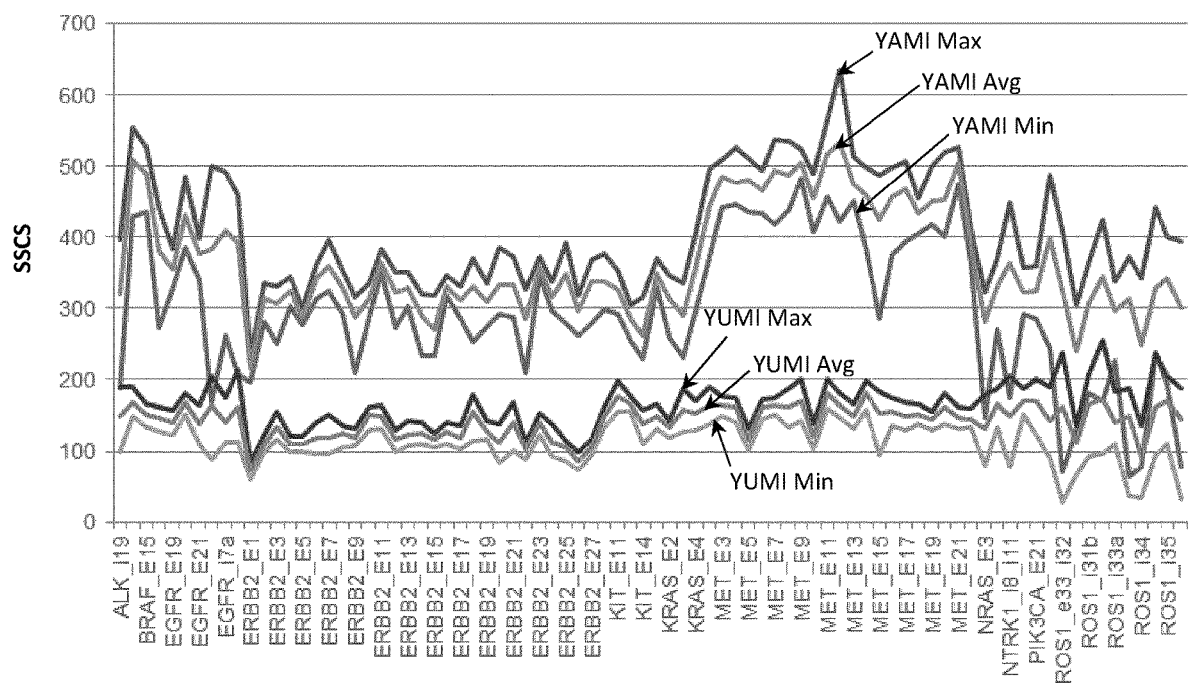
FIG. 5 shows the 'single-strand consensus sequences' (SSCS) that were derived for certain exon or intron regions of several cancer-related genes when cfDNA libraries were generated using YAMIs.
Figure 7:
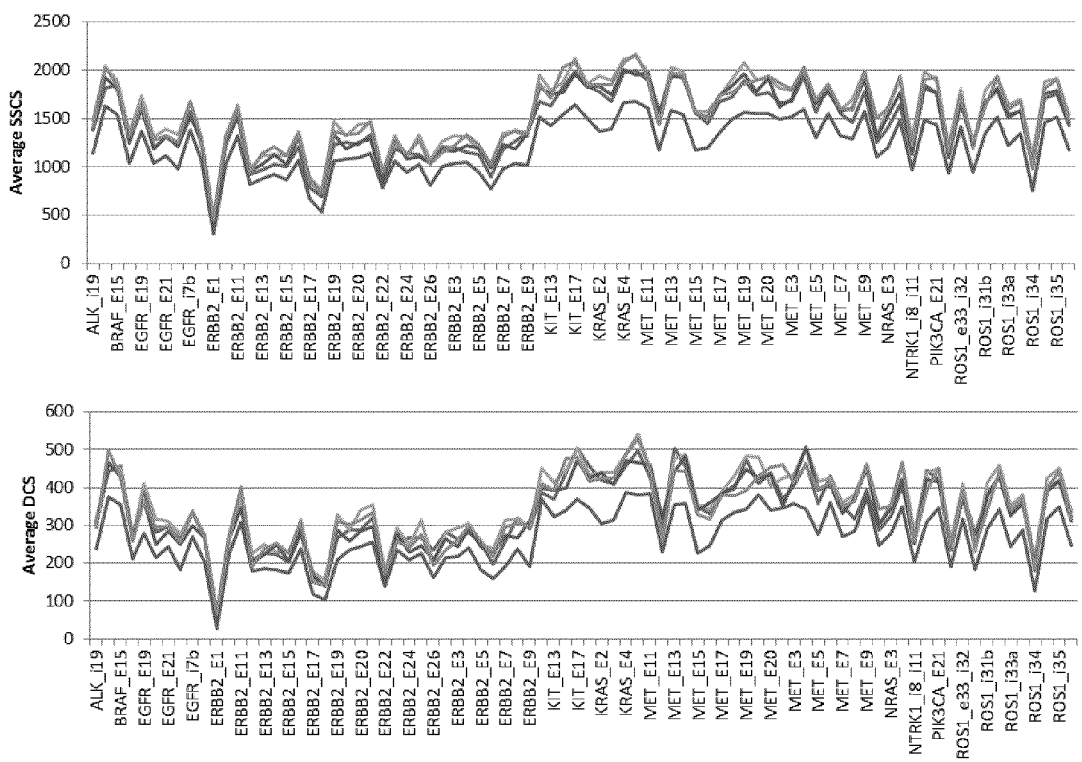
FIG. 7 shows the average SSCS and average duplex consensus sequences (DCS) that were derived for certain exon or intron regions of several cancer-related genes when libraries were generated with 5 ng cfDNA input from five patient samples using short YAMIs (shYAMIs) represented by SEQ ID NOS: 1-48.

Indeed, the elevated ligation efficiency of the YAMIs resulted in an observable increase in the overall read depth and complexity of the cfDNA libraries generated with YAMIs compared to that observed with YUMIs (see FIG. 4). FIG. 5 demonstrates that a greater number of 'single-strand consensus sequences' (SSCS) were derived for various exon or intron regions of cancer-related genes when cfDNA libraries were generated using YAMIs compared to YUMIs. Further, FIG. 7 shows that approximately 500-1800 single strand consensus reads (SSCS) within target gene regions were obtained from cfDNA input levels as low as 5 ng when cfDNA libraries were generated using short YAMIs (shYA-MIs) (represented by SEQ ID NOS: 1-48).

These results demonstrate that the Y-shaped nucleic acid adapters of the present technology (YAMIs and shYAMIs) show superior efficacy with respect to generating complex DNA libraries from limited amounts of input DNA, particularly cfDNA, compared to other Y-shaped adapters known in the art (e.g., YAMIs). Accordingly, the Y-shaped nucleic acid adapters of the present technology are useful in methods for detecting mutations in circulating tumor DNA (ctDNA) molecules present in patient samples.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A nucleic acid adapter comprising a first oligonucleotide strand and a second oligonucleotide strand, wherein
   (a) the first oligonucleotide strand
      (i) comprises a first proximal region and a first distal region, wherein the first proximal region comprises a first unique molecular identifier sequence and a first spacer sequence having the sequence 5' TGACT 3' (SEQ ID NO: 49), wherein the first spacer sequence is located 3' to the first unique molecular identifier sequence and wherein the "T" nucleotide located at the 3' end of the first spacer sequence (SEQ ID NO: 49) contains a phosphorothioate bond; and
      (ii) does not comprise a degenerate or semi-degenerate sequence;
   (b) the second oligonucleotide strand
      (i) comprises a second proximal region and a second distal region, wherein the second proximal region comprises a second unique molecular identifier sequence and a second spacer sequence having the sequence 5' GTCA 3' (SEQ ID NO: 50), wherein the spacer sequence is located 5' to the second unique molecular identifier; and
      (ii) does not comprise a degenerate or semi-degenerate sequence;
   (c) the first proximal region of the first oligonucleotide strand hybridizes with the second proximal region of the second oligonucleotide strand; and
   (d) the first distal region of the first oligonucleotide strand does not hybridize with the second distal region of the second oligonucleotide strand,
wherein the nucleotide sequence of the second oligonucleotide strand is selected from the group consisting of:
   5' GTCAGCTACTGCAGCTAGATCGAAGAGCACACGTCTGAACTCCAG TCAC 3' (SEQ ID NO: 2);
   5' GTCAGTATCATCATCAAGATCGAAGAGCACACGTCTGAACTCCAG TCAC 3' (SEQ ID NO: 4);
   5' GTCACTCGACAGTCGAAGATCGAAGAGCACACGTCTGAACTCCAG TCAC 3' (SEQ ID NO: 6);
   5' GTCATAGCTAGAGTACAGATCGAAGAGCACACGTCTGAACTCCAG TCAC 3' (SEQ ID NO: 8);
   5' GTCAACGAGTGCTCTGAGATCGAAGAGCACACGTCTGAACTCCAG TCAC 3' (SEQ ID NO: 10);
   5' GTCAGACTATCGCATGAGATCGAAGAGCACACGTCTGAACTCCAG TCAC 3' (SEQ ID NO: 12);
   5' GTCACTCGACTGATGAAGATCGAAGAGCACACGTCTGAACTCCAG TCAC 3' (SEQ ID NO: 14);
   5' GTCAATACCGCTGATTAGATCGAAGAGCACACGTCTGAACTCCAG TCAC 3' (SEQ ID NO: 16);
   5' GTCACAGTAGTATGCTAGATCGGAAGAGCACACGTCTGAACTCCAG TCAC 3' (SEQ ID NO: 18);
   5' GTCAACGTGTATCAGCAGATCGGAAGAGCACACGTCTGAACTCCAGTCAC 3' (SEQ ID NO: 20);
   5' GTCACGTGTGACAGAGAGATCGGAAGAGCACACGTCTGAACTCCAG TCAC 3' (SEQ ID NO: 22);
   5' GTCATGATGACGTAGCAGATCGGAAGAGCACACGTCTGAACTCCAG TCAC 3' (SEQ ID NO: 24);
   5' GTCAAGTGACATCTGCAGATCGGAAGAGCACACGTCTGAACTCCAG TCAC 3' (SEQ ID NO: 26);
   5' GTCACTAGCTGTGAGTAGATCGGAAGAGCACACGTCTGAACTCCAG TCAC 3' (SEQ ID NO: 28);
   5' GTCATACATGAGCGAGAGATCGGAAGAGCACACGTCTGAACTCCAG TCAC 3' (SEQ ID NO: 30);
   5' GTCACTAGTGCAGCTAAGATCGGAAGAGCACACGTCTGAACTCCAG TCAC 3' (SEQ ID NO: 32);
   5' GTCATAGCTCGAACTGAGATCGGAAGAGCACACGTCTGAACTCCAG TCAC 3' (SEQ ID NO: 34);
   5' GTCAGCGAGTCATGCAAGATCGGAAGAGCACACGTCTGAACTCCAG TCAC 3' (SEQ ID NO: 36);
   5' GTCATGTACAGTACACAGATCGGAAGAGCACACGTCTGAACTCCAG TCAC 3' (SEQ ID NO: 38);
   5' GTCATCAGACTCTAGTAGATCGGAAGAGCACACGTCTGAACTCCAG TCAC 3' (SEQ ID NO: 40);
   5' GTCAGACACGCACTCTAGATCGGAAGAGCACACGTCTGAACTCCAG TCAC 3' (SEQ ID NO: 42);
   5' GTCAATCTGATGCGTAAGATCGGAAGAGCACACGTCTGAACTCCAG TCAC 3' (SEQ ID NO: 44);
   5' GTCAACTGTCATGCAGAGATCGGAAGAGCACACGTCTGAACTCCAG TCAC 3' (SEQ ID NO: 46); and
   5' GTCAGTGAGATCGTACAGATCGGAAGAGCACACGTCTGAACTCCAG TCAC 3' (SEQ ID NO: 48), and
wherein the nucleic acid adapter is configured to efficiently ligate to cfDNA molecules at input concentrations as low as 5 ng.

2. The nucleic acid adapter of claim 1, wherein the first unique molecular identifier sequence of the first oligonucleotide strand is selected from the group consisting of: 5' AGCTGCAGTAGC 3' (SEQ ID NO: 51); 5' TGATGATGATAC 3' (SEQ ID NO: 52); 5' TCGACTGTCGAG 3' (SEQ ID NO: 53); 5' GTACTCTAGCTA 3' (SEQ ID NO: 54); 5' CAGAGCACTCGT 3' (SEQ ID NO: 55); 5' CATGCGATAGTC 3' (SEQ ID NO: 56); 5' TCATCAGTCGAG 3' (SEQ ID NO: 57); 5' AATCAGCGGTAT 3' (SEQ ID NO: 58); 5' AGCATACTACTG 3' (SEQ ID NO: 59); 5' GCTGATACACGT 3' (SEQ ID NO: 60); 5' CTCTGTCACACG 3' (SEQ ID NO: 61); 5' GCTACGTCATCA 3' (SEQ ID NO: 62); 5' GCAGATGTCACT 3' (SEQ ID NO: 63); 5' ACTCACAGCTAG 3' (SEQ ID NO: 64); 5' CTCGCTCATGTA 3' (SEQ ID NO: 65); 5' TAGCTGCACTAG 3' (SEQ ID NO: 66); 5' CAGTTCGAGCTA 3' (SEQ ID NO: 67); 5' TGCATGACTCGC 3' (SEQ ID NO: 68); 5' GTGTACTGTACA 3' (SEQ ID NO: 69); 5' ACTAGAGTCTGA 3' (SEQ ID NO: 70); 5' AGAGTGCGTGTC 3' (SEQ ID NO: 71); 5' TACGCATCAGAT 3' (SEQ ID NO: 72); 5' CTGCATGACAGT 3' (SEQ ID NO: 73); and 5' GTACGATCTCAC 3' (SEQ ID NO: 74).

3. The nucleic acid adapter of claim 1, wherein the second unique molecular identifier sequence of the second oligonucleotide strand is selected from the group consisting of: 5' GCTACTGCAGCT 3' (SEQ ID NO: 75); 5' GTATCATCATCA 3' (SEQ ID NO: 76); 5' CTCGACAGTCGA 3' (SEQ ID NO: 77); 5' TAGCTAGAGTAC 3' (SEQ ID NO: 78); 5' ACGAGTGCTCTG 3' (SEQ ID NO: 79); 5' GACTATCGCATG 3' (SEQ ID NO: 80); 5' CTCGACTGATGA 3' (SEQ ID NO: 81); 5' ATACCGCTGATT 3' (SEQ ID NO: 82); 5' CAGTAGTATGCT 3' (SEQ ID NO: 83); 5' ACGTGTATCAGC 3' (SEQ ID NO: 84); 5' CGTGTGACAGAG 3' (SEQ ID NO: 85); 5' TGATGACGTAGC 3' (SEQ ID NO: 86); 5' AGTGACATCTGC 3' (SEQ ID NO: 87); 5' CTAGCTGTGAGT 3' (SEQ ID NO: 88); 5' TACATGAGCGAG 3' (SEQ ID NO: 89); 5' CTAGTGCAGCTA 3' (SEQ ID NO: 90); 5' TAGCTCGAACTG 3' (SEQ ID NO: 91); 5' GCGAGTCATGCA 3' (SEQ ID NO: 92); 5' TGTACAGTACAC 3' (SEQ ID NO: 93); 5' TCAGACTCTAGT 3' (SEQ ID NO: 94); 5' GACACGCACTCT 3' (SEQ ID NO: 95); 5' ATCTGATGCGTA 3' (SEQ ID NO: 96); 5' ACTGTCATGCAG 3' (SEQ ID NO: 97); and 5' GTGAGATCGTAC 3' (SEQ ID NO: 98).

4. The nucleic acid adapter of claim 1, wherein the nucleotide sequence of the first oligonucleotide strand is selected from the group consisting of:
    5' TACACTCTTTCCCTACACGACGCTCTTCCGATCTAGCTGCAGTAGCT GACT 3' (SEQ ID NO: 1);
    5' TACACTCTTTCCCTACACGACGCTCTTCCGATCTTGATGATGATACT GACT 3' (SEQ ID NO: 3);
    5' TACACTCTTTCCCTACACGACGCTCTTCCGATCTTCGACTGTCGAGT GACT 3' (SEQ ID NO: 5);
    5' TACACTCTTTCCCTACACGACGCTCTTCCGATCTGTACTCTAGCTAT GACT 3' (SEQ ID NO: 7);
    5' TACACTCTTTCCCTACACGACGCTCTTCCGATCTCAGAGCACTCGTT GACT 3' (SEQ ID NO: 9);
    5' TACACTCTTTCCCTACACGACGCTCTTCCGATCTCATGCGATAGTCT GACT 3' (SEQ ID NO: 11);
    5' TACACTCTTTCCCTACACGACGCTCTTCCGATCTTCATCAGTCGAGT GACT 3' (SEQ ID NO: 13);
    5' TACACTCTTTCCCTACACGACGCTCTTCCGATCTAATCAGCGGTATT GACT 3' (SEQ ID NO: 15);
    5' TACACTCTTTCCCTACACGACGCTCTTCCGATCTAGCATACTACTGT GACT 3' (SEQ ID NO: 17);
    5' TACACTCTTTCCCTACACGACGCTCTTCCGATCTGCTGATACACGTT GACT 3' (SEQ ID NO: 19);
    5' TACACTCTTTCCCTACACGACGCTCTTCCGATCTCTCTGTCACACGT GACT 3' (SEQ ID NO: 21);
    5' TACACTCTTTCCCTACACGACGCTCTTCCGATCTGCTACGTCATCAT GACT 3' (SEQ ID NO: 23);
    5' TACACTCTTTCCCTACACGACGCTCTTCCGATCTGCAGATGTCACTT GACT 3' (SEQ ID NO: 25);
    5' TACACTCTTTCCCTACACGACGCTCTTCCGATCTACTCACAGCTAGT GACT 3' (SEQ ID NO: 27);
    5' TACACTCTTTCCCTACACGACGCTCTTCCGATCTCTCGCTCATGTATG ACT 3' (SEQ ID NO: 29);
    5' TACACTCTTTCCCTACACGACGCTCTTCCGATCTTAGCTGCACTAGT GACT 3' (SEQ ID NO: 31);
    5' TACACTCTTTCCCTACACGACGCTCTTCCGATCTCAGTTCGAGCTAT GACT 3' (SEQ ID NO: 33);
    5' TACACTCTTTCCCTACACGACGCTCTTCCGATCTTGCATGACTCGCT GACT 3' (SEQ ID NO: 35);
    5' TACACTCTTTCCCTACACGACGCTCTTCCGATCTGTGTACTGTACAT GACT 3' (SEQ ID NO: 37);
    5' TACACTCTTTCCCTACACGACGCTCTTCCGATCTACTAGAGTCTGAT GACT 3' (SEQ ID NO: 39);
    5' TACACTCTTTCCCTACACGACGCTCTTCCGATCTAGAGTGCGTGTCT GACT 3' (SEQ ID NO: 41);
    5' TACACTCTTTCCCTACACGACGCTCTTCCGATCTTACGCATCAGATT GACT 3' (SEQ ID NO: 43);
    5' TACACTCTTTCCCTACACGACGCTCTTCCGATCTCTGCATGACAGTT GACT 3' (SEQ ID NO: 45); and
    5' TACACTCTTTCCCTACACGACGCTCTTCCGATCTGTACGATCTCACT GACT 3' (SEQ ID NO: 47).

5. The nucleic acid adapter of claim 1, wherein the 5' end of the first oligonucleotide strand or the 3' end of the second oligonucleotide strand is labelled with biotin.

6. The nucleic acid adapter of claim 1, wherein the nucleic acid adapter is used to sequence a double-stranded target nucleic acid molecule selected from the group consisting of double-stranded DNA or double-stranded RNA.

7. The nucleic acid adapter of claim 1, further comprising at least two PCR primer binding sites, at least two sequencing primer binding sites, a 2-20 base pair sample-specific barcode sequence, or any combination thereof.

8. The nucleic acid adapter of claim 6, wherein the double-stranded DNA is sheared genomic DNA, or cell-free DNA.

9. A method for detecting at least one mutation in a double-stranded circulating tumor DNA (ctDNA) molecule present in a sample obtained from a patient comprising
    (a) ligating a plurality of Y-shaped adapters to both ends of the double-stranded ctDNA molecule to form a double-stranded adapter-ctDNA complex, each Y-shaped adapter comprising a first oligonucleotide strand and a second oligonucleotide strand, wherein the sequence of the first oligonucleotide strand and the sequence of the second oligonucleotide strand are selected from the group consisting of SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 33 and SEQ ID NO: 34; SEQ ID NO: 35 and SEQ ID NO: 36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 45 and SEQ ID NO: 46; and SEQ ID NO: 47 and SEQ ID NO: 48;

(b) amplifying both strands of the adapter-ctDNA complex to produce first amplicons and second amplicons, wherein the first amplicons are derived from the first oligonucleotide strand, and the second amplicons are derived from the second oligonucleotide strand;

(c) sequencing the first and second amplicons;

(d) detecting at least one mutation in the double-stranded ctDNA molecule, when a mutation detected in the first amplicons is consistent with a mutation detected in the second amplicons.

10. The method of claim 9, further comprising enriching the first amplicons and second amplicons with a plurality of bait sequences, wherein the plurality of bait sequences comprises at least one gene region that corresponds to each of a plurality of cancer-related genes.

11. The method of claim 10, wherein the plurality of cancer-related genes comprises ALK, BRAF, EGFR, ERBB2, KIT, KRAS, MET, NRAS, NTRK1, PIK3CA, ROS1, and RET.

12. The method of claim 9, wherein the plurality of bait sequences are RNA baits, DNA baits, or a mixture of RNA baits and DNA baits.

13. The method of claim 12, wherein the plurality of bait sequences comprises a 1:1 mixture of RNA baits and DNA baits.

14. The method of claim 9, wherein both of the 3' ends of the double-stranded ctDNA molecule further comprise an A-overhang.

15. The method of claim 9, wherein each Y-shaped adapter further comprises at least two sequencing primer binding sites, or a biotin label, or a patient-specific barcode sequence, wherein the patient-specific barcode sequence comprises 2-20 nucleotides.

16. The method of claim 9, wherein the sample comprises no more than 5 ng or at least 6-30 ng of cell-free DNA.

17. The method of claim 9, wherein the sample is whole blood, serum, plasma, synovial fluid, lymphatic fluid, ascites fluid, or interstitial fluid.

18. The method of claim 9, wherein the patient is diagnosed with ovarian cancer, breast cancer, colon cancer, lung cancer, prostate cancer, gastric cancer, pancreatic cancer, cervical cancer, liver cancer, bladder cancer, cancer of the urinary tract, thyroid cancer, renal cancer, carcinoma, melanoma, head and neck cancer, or brain cancer.

* * * * *